United States Patent
Salvino et al.

(10) Patent No.: US 11,717,212 B2
(45) Date of Patent: Aug. 8, 2023

(54) CERVIX CALIPER

(71) Applicants: Chris Salvino, Scottsdale, AZ (US); Keir Hart, Lafayette, CO (US); Mark J. Huseman, Broomfield, CO (US)

(72) Inventors: Chris Salvino, Scottsdale, AZ (US); Keir Hart, Lafayette, CO (US); Mark J. Huseman, Broomfield, CO (US)

(73) Assignee: SharpMed, LLC., Scottdale, AZ (US)

( * ) Notice: Subject to any disclaimer, the term of this patent is extended or adjusted under 35 U.S.C. 154(b) by 619 days.

(21) Appl. No.: 16/867,700

(22) Filed: May 6, 2020

(65) Prior Publication Data

US 2021/0345940 A1 Nov. 11, 2021

(51) Int. Cl.
A61B 5/00 (2006.01)
A61B 5/107 (2006.01)
A61B 42/10 (2016.01)
G01B 3/00 (2006.01)

(52) U.S. Cl.
CPC ............ *A61B 5/435* (2013.01); *A61B 5/1076* (2013.01); *A61B 5/6826* (2013.01); *A61B 5/6831* (2013.01); *A61B 42/10* (2016.02); *G01B 3/00* (2013.01)

(58) Field of Classification Search
CPC ..... A61B 5/435; A61B 5/1076; A61B 5/6826; A42B 42/10; G01B 3/00; G01B 3/24
See application file for complete search history.

(56) References Cited

U.S. PATENT DOCUMENTS

| | | | |
|---|---|---|---|
| 4,207,902 A | 6/1980 | Krementsov | |
| 4,245,656 A | 1/1981 | Farr et al. | |
| 4,362,167 A | 12/1982 | Nicolai et al. | |
| 4,611,603 A | 9/1986 | Kelso et al. | |
| 4,682,609 A | 7/1987 | Parsons | |
| 5,658,295 A * | 8/1997 | Krementsov | A61B 5/435 606/119 |
| 6,066,104 A | 5/2000 | Dao et al. | |
| 7,150,108 B2 | 12/2006 | Babb | |
| 7,654,970 B2 | 2/2010 | Dubey et al. | |
| 8,439,850 B2 | 5/2013 | Sherts et al. | |
| 2007/0213640 A1 | 9/2007 | Mansour et al. | |
| 2010/0049094 A1 | 2/2010 | O'Brien et al. | |
| 2015/0148809 A1* | 5/2015 | Bailey | A61B 5/4566 606/102 |
| 2016/0270714 A1 | 9/2016 | Martin et al. | |
| 2022/0202407 A1* | 6/2022 | Agrawal | A61B 5/01 |

\* cited by examiner

*Primary Examiner* — Devin B Henson
(74) *Attorney, Agent, or Firm* — Kenneth Altshuler

(57) ABSTRACT

Disclosed are embodiments describing finger calipers with a pair of lever arms pivotally attached to a hand plate via a pivot point at their respective proximal ends. Each of the lever arms extend along the length of a finger and attach to the end of the respective finger via a finger cuff or some other attachment means. Accordingly, the lever arms can open and close, or otherwise splay apart, in a scissor like manner when the fingers that they are attached to open and close or otherwise splay apart. A ratchet system comprised by one of the lever arms and the hand plate allow for one-way motion of the ratcheted lever arm. The other lever arm freely pivots across the hand plate. When a medical examiner is using the finger calipers, they can reliably measure a dilated cervix by reading a corresponding dilation measurement indicium associated with the ratcheted lever arm.

20 Claims, 26 Drawing Sheets

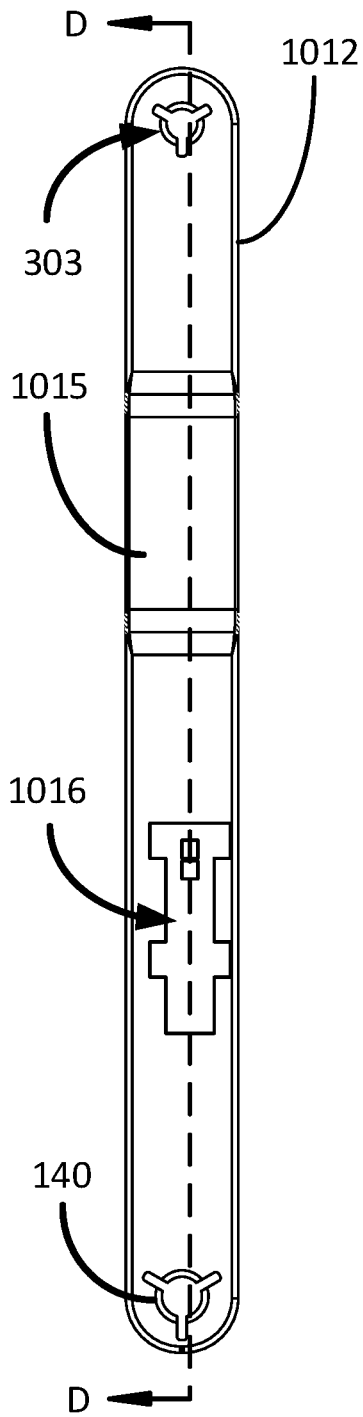 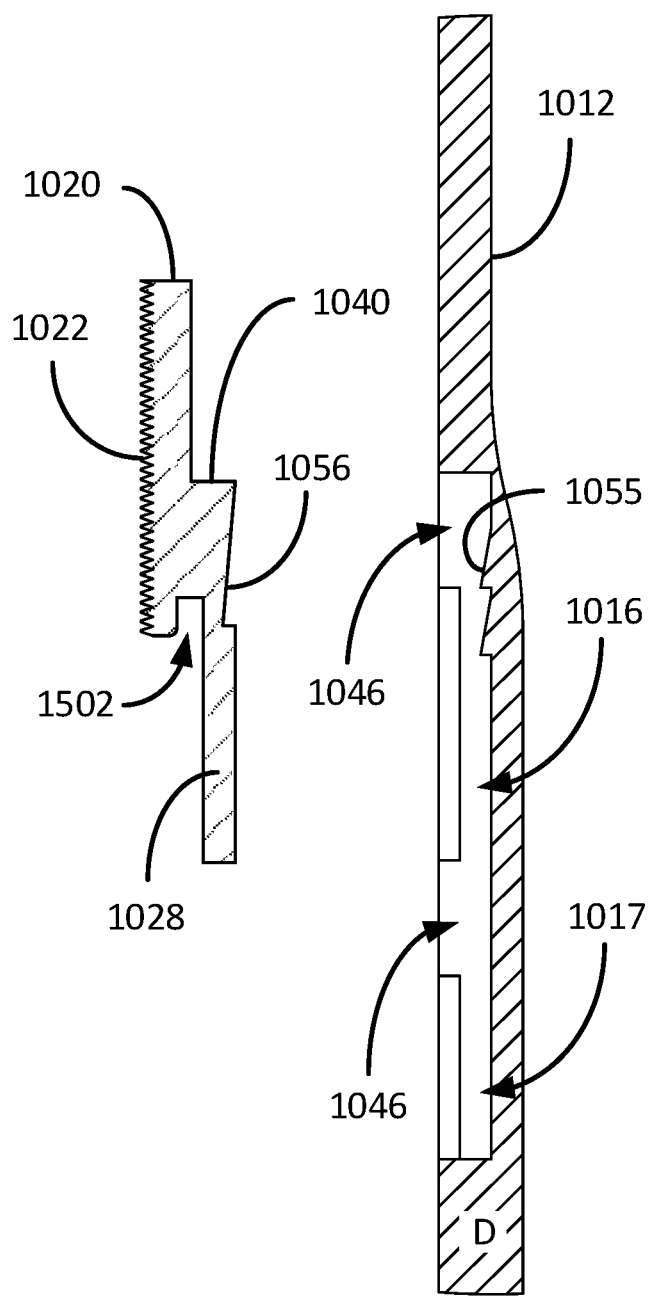
FIG. 14A  FIG. 14B

CERVIX CALIPER

CROSS-REFERENCE TO RELATED APPLICATIONS

None

FIELD OF THE INVENTION

The present embodiments are directed to finger calipers used to measure a woman's dilated cervix.

DESCRIPTION OF RELATED ART

Evaluating cervical dilation is widely considered a highly important parameter when managing the delivery phase of childbirth. Despite the variety of accurate cervical dilation measurement devices presently available, medical professionals prefer and typically only use the age-old method of spreading their index and a second finger (typically a middle finger) across the dilated cervix to guess the diameter of dilation. However, there is high variability of accurately determining the diameter of cervical dilation when guessing how far fingers are spread apart while feeling a patient's cervix. Inaccurately evaluating cervical dilation can lead to premature C-sections, administration of drugs and other actions that are otherwise unnecessary thereby incurring systemic costs and putting both mother and child at risk. Accordingly, there is a need to more accurately determine cervix dilation in a manner that arguments present day techniques.

It is to innovations related to this subject matter that the embodiments of the invention is generally directed.

SUMMARY OF THE INVENTION

The present embodiments are directed to cervix measurement calipers that incorporate present day use of obstetrician fingers for evaluating cervical dilation.

Certain embodiments of the present invention contemplate cervix dilation measurement calipers comprising: a first finger lever arm pivotally attached to a palm plate in a first proximal region of the first finger lever arm via a pivot point; a second finger lever arm pivotally attached to the palm plate in a second proximal region of the second finger lever arm via the pivot point; a first finger cuff attached to a first distal region of the first finger lever arm, the first finger cuff configured to capture a first human finger; a second finger cuff attached to a second distal region of the second finger lever arm, the second finger cuff and configured to capture a second human finger; at least one male ratchet protrusion extending from the first finger lever arm, the male ratchet protrusion in cooperation with one of a plurality of female ratchet recessions in the palm plate, the first finger lever arm pivotally movable across the palm plate in only one direction because of the male ratchet protrusion in cooperation with the female ratchet recession; and graduated indicia displayed in a path following the plurality of female ratchet recessions, the graduated indicia corresponding to different dilated cervix diameters, one of the graduated indicia configured to be singled out via the first finger lever arm when the cervix dilation measurement calipers are splayed to measure one of the different dilated cervix diameters.

Other certain embodiments of the present invention contemplate a method comprising: providing a cervix caliper possessing: a first finger arm having a first arm attachment end and a free end, a second finger arm having a second arm attachment end and a free end, the finger arms pivotally attached to a palm plate at a pivot point at the attachment ends; capturing a first finger in a first finger cuff, the first finger cuff attached to a first free end region of the first free end; capturing a second finger in a second finger cuff, the second finger cuff attached to a second free end region of the second free end; after the capturing steps, opening the cervix calipers in a scissor motion by spreading the first finger and the second finger apart to touch a dilated cervix at approximately a largest diameter across the dilated cervix; reading an indicium singled out from a set of graduated indicia on the graduated palm plate, the indicium singled out via a one-way ratchet comprised by a male ratchet portion on the first finger arm and a female portion on the palm plate.

Yet other certain embodiments of the present invention contemplate cervix dilation calipers comprising: a graduated palm plate possessing on a first plate side a female ratchet portion and a plurality of graduated indicia; an index finger lever arm pivotally attached to the first plate side at a pivot point in the graduated palm plate, a male portion engaged with the female ratchet portion and at least one of the graduated indicia viewable via a window in the index finger lever arm; a second finger lever arm pivotally attached to a second plate side of the graduated palm plate at the pivot point, the cervix dilation calipers configured to splay the index finger lever arm and the second finger lever arm apart like scissors; a first finger cuff attached to an index finger distal end of the index finger lever arm; and a second finger cuff attached to a second finger distal end of the second finger lever arm.

BRIEF DESCRIPTION OF THE DRAWINGS

FIGS. 14A and 14B are line drawings of a front view second finger lever arm and cross-section of the second finger lever arm in relation to the locking slider consistent with embodiments of the present invention.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of instruments and situations involving aspects of the inventive concepts of the disclosed cervix dilation evaluation finger caliper/s. In what follows, similar or identical structures may (and may not) be identified using identical callouts.

Certain embodiments of the present invention generally relate to cervix measurement calipers that incorporate present day use of obstetrician fingers for evaluating cervical dilation. It is fairly well established that measuring a dilated cervix is preferably done using a medical examiner's fingers. Disclosed herein are embodiments describing finger calipers with a pair of lever arms pivotally attached to a hand plate via a pivot point at their respective proximal ends. Each of the lever arms extend along the length of a finger and attach to the end of the respective finger via a finger cuff or some other attachment means. Accordingly, the lever arms can open and close, or otherwise splay apart, in a scissor like manner when the fingers that they are attached to, open and close or otherwise splay apart. A ratchet system comprised by one of the lever arms and the hand plate allow for one-way motion of the ratcheted lever arm. The other lever arm freely pivots across the hand plate. When a medical examiner is using the finger calipers, they can reliably measure a dilated cervix by reading a corresponding dilation measurement indicium associated with the ratcheted lever arm. Because the hand plate can float over the medical examiner's palm, either high on the palm or low on the palm near the wrist, consistent cervical measurements can be taken no matter how large or small the hand.

A detailed description in view of the associated figures illustrating examples of the inventive concepts are presented below.

Figure 1A:
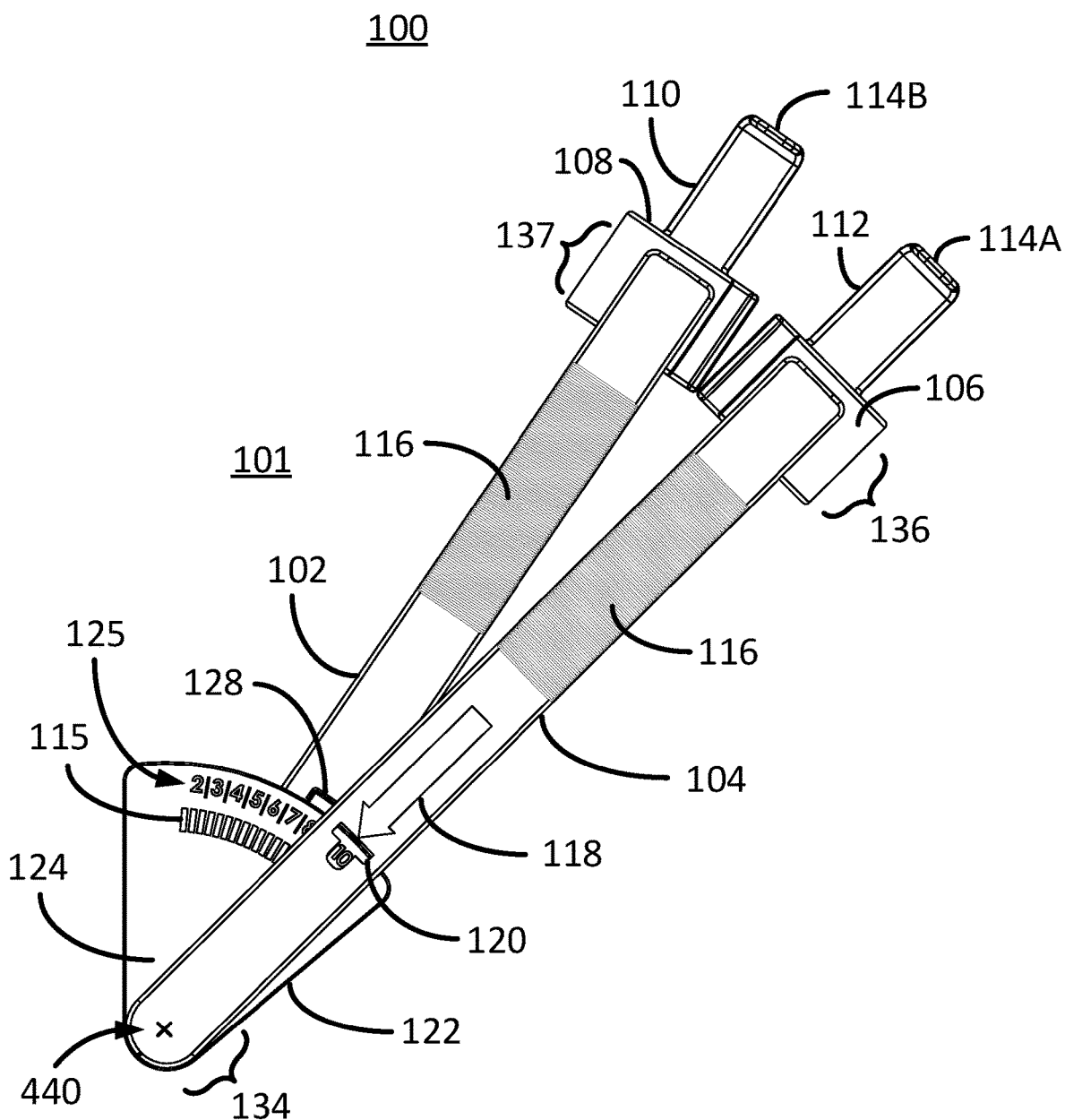
FIGS. 1A-1E illustratively depict line drawings of various perspectives of cervical finger caliper arrangement, or simply finger caliper arrangement, consistent with embodiments of the present invention.

FIGS. 1A-1E illustratively depict line drawings of various perspectives of cervical finger calipers arrangement, or simply finger calipers arrangement, consistent with embodiments of the present invention. FIG. 1A illustratively show (an embodiment 100 of finger calipers) a finger caliper embodiment 100 as viewed when looking at the palm 600 of a human hand 602 (see FIG. 2), which for purposes of the description is considered the caliper front side 101. The basic components of the finger caliper 100 include a graduated hand/palm plate 122, an index finger lever arm 104, and a second finger lever arm 102. The index finger lever arm 104 and the second finger lever arm 102 are pivotally attached to the graduated palm plate 122 at their respective proximal regions 134. Certain embodiments contemplate the proximal region 134 being the lower 10% of the index finger lever arm 104, and 10% of the second finger lever arm 102.

The front surface/side 124 of the graduated palm plate 122 is essentially defined as being viewable via the calipers front side 101, and generally comprises a female ratchet portion 115 and a plurality of graduated indicia 125. In the present embodiment, the graduated indicia 125 correspond with the number centimeters that a cervix (not shown) is dilated (i.e., the greatest diameter of the dilated cervix) when measured with the finger calipers 100. The index finger lever arm 104 extends from a pivot point 440 to a distal index finger region 136 (which is the free distal end region) where a first finger cuff 106 is attached. The first finger cuff 106 is a semicircular cuff that at least partially encircles a human index finger distal phalange. As shown, an index fingertip extender 112 extends distally from the first finger cuff 106 and terminates at a fingertip cap 114A, which in the present embodiment is a 90° bend that covers at least a portion of a human fingertip. The index finger lever arm 104 comprises a window 120 that makes viewable at least one of the graduated indicia 125. Certain embodiments envision a single graduated indicium 125 viewable through the window 120. In the present embodiment, a dilation measurement arrow 118 pointing to the window 120, and therefore the graduated indicium 125, provides a quick visual of the specific graduated indicium 125 corresponding to the cervical diameter in centimeters when dilated. In the present figure, the dilation measurement arrow 118 shows a 10 corresponding to a 10 cm dilated cervix. The second finger lever arm 102 extends from the pivot point 440 to a distal second finger region 137 where a second finger cuff 108 is attached. The second finger cuff 108 is also a semicircle cuff that at least partially encircles a second human finger distal phalange. As shown, a second fingertip extender 110 extends distally from the second finger cuff 108 and terminates at a fingertip cap 114B, which in the present embodiment is a 90° bend that covers at least a portion of a human fingertip. Both the index finger lever arm 104 and the second finger lever arm 102 comprise finger bending grooves 116 that permit the lever arms 102 and 104 to more easily bend with human fingers.

Figure 1B:
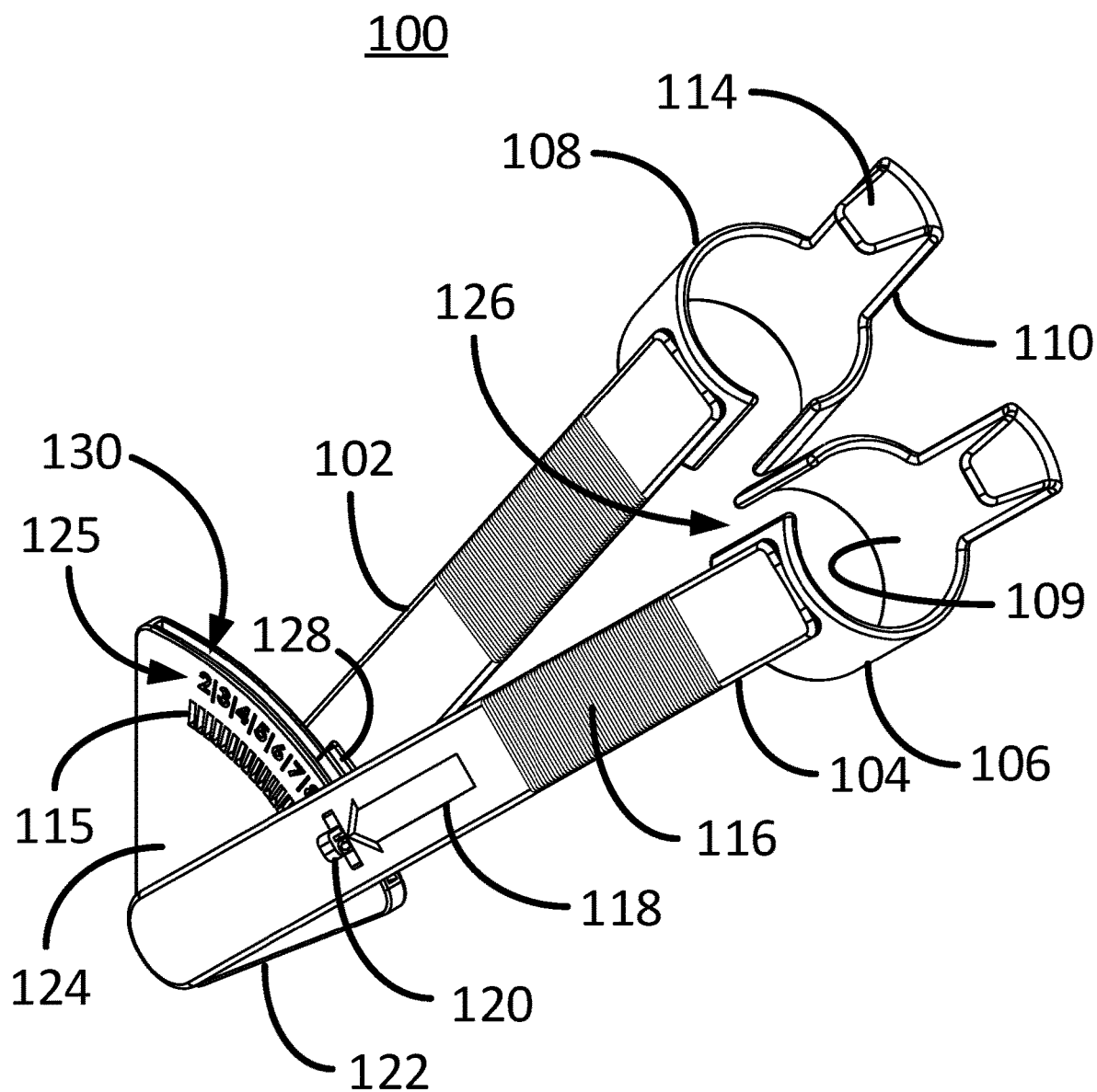

FIG. 1B illustratively depicts a line drawing of a perspective view of the finger calipers 100. This view better depicts the semicircular first finger cuff 106 and second finger cuff 108, whereby each of the finger cuffs 106 and 108 completes no more than 270° of a circle with a slot 126 that is no less than 90° of a circle. Other embodiments envision finger cuffs 106 and 108 completing less than 360° of a circle with a slot making up the balance of the circle. Yet other embodiments envision finger cuffs making up less than 180° of a circle. While even other embodiments envision finger cuffs comprising adhesive on the inner surface 109 configured to adhere to a human finger. In certain embodiments, each finger cuff 106 and 108 is composed of a flexible material, such as PVC, that provides flexibility to enlarge the slot 126 by spring force to accommodate different diameter fingers to fit within the cuffs 106 and 108. As further seen from this angle, the fingertip caps 114A/B are positioned to cover at least one of the fingertips engaged with the cuffs 106 and 108 to hold the calipers 100 in position relative to an index finger and a secondary finger. Also shown here is a second finger retention tab 128 that slidingly engages in a palm plate slot 130, which tracks the second finger lever arm 102 (and index finger lever arm 104) along the palm plate 122.

Figure 1C:
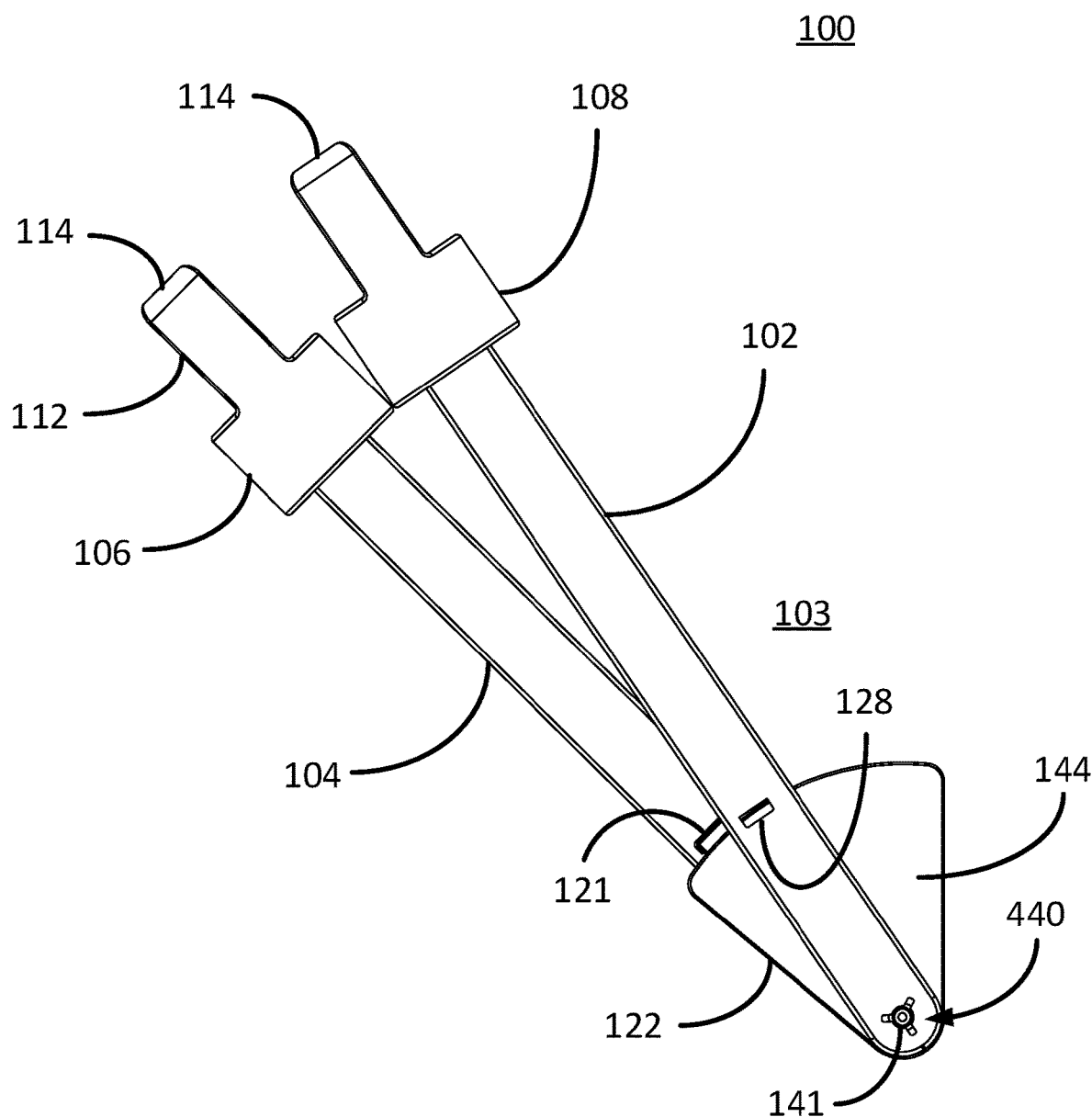

FIG. 1C illustratively shows a line drawing of a palm facing view of the finger caliper embodiment 100, which for purposes of description is considered the calipers' back side 103. In this embodiment, the lever arms 102 and 104 are pivotally attached together via a pin (not shown) and retaining lock ring 141 at the pivot point 440. Both the second finger retention tab 128 and the index finger retention tab 121 are shown from this view 103. For reference, the graduated palm plate back surface/side 144 (the palm side, the side that touches a human palm) of palm plate 122 is presented in this view.

Figure 1D:
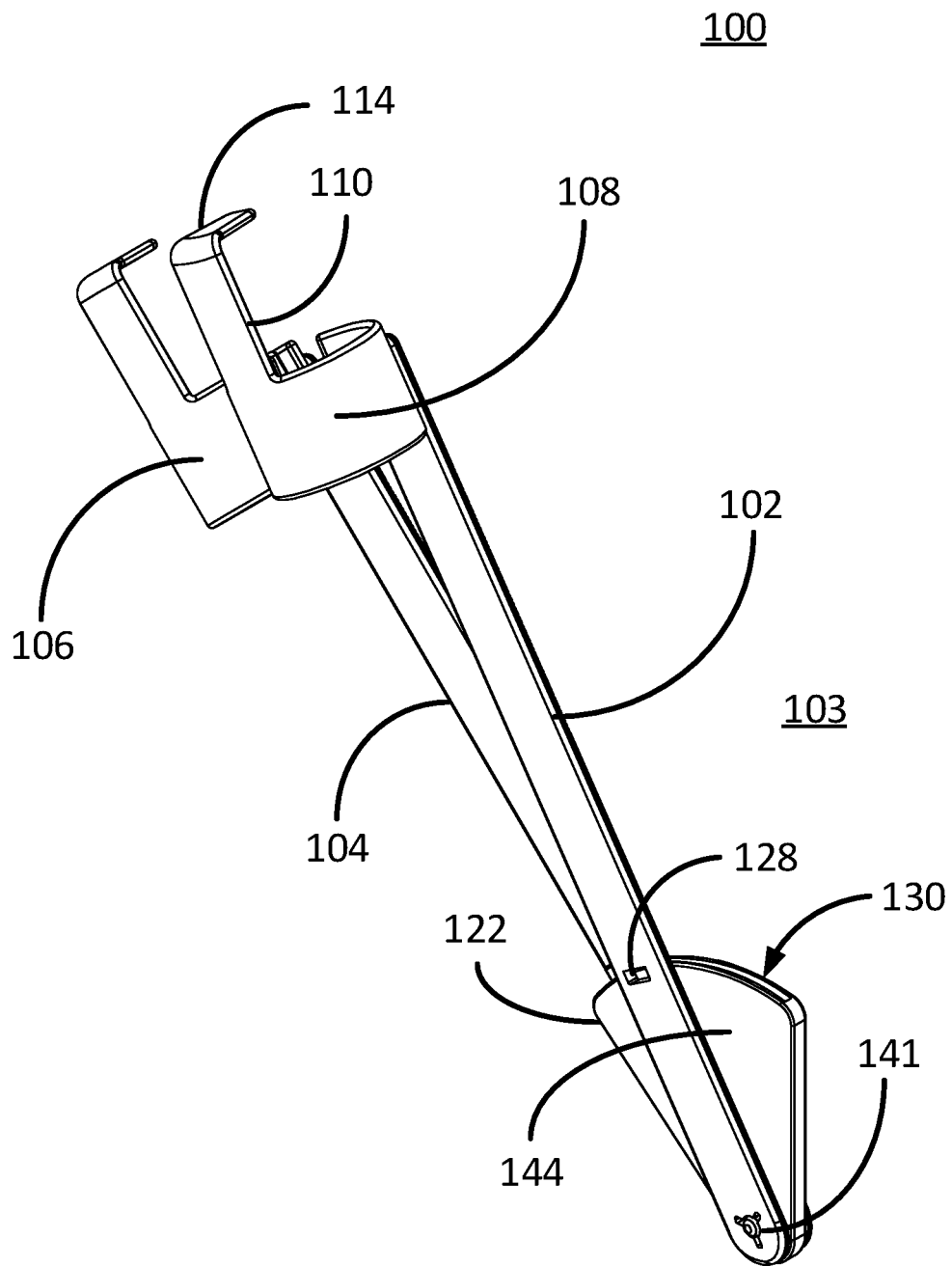

FIG. 1D illustratively depicts a line drawing of a perspective view of the calipers' back side 103 showing the palm plate slot 130 and the 90° bend leading into the fingertip caps 114. It is further pointed out that in the present finger caliper embodiment 100, neither lever arms 102 and 104 possess any finger bending grooves 116 on the caliper back side 103 because the lever arms 102 and 104 need only curl in the direction of the front side 101.

Figure 1E:
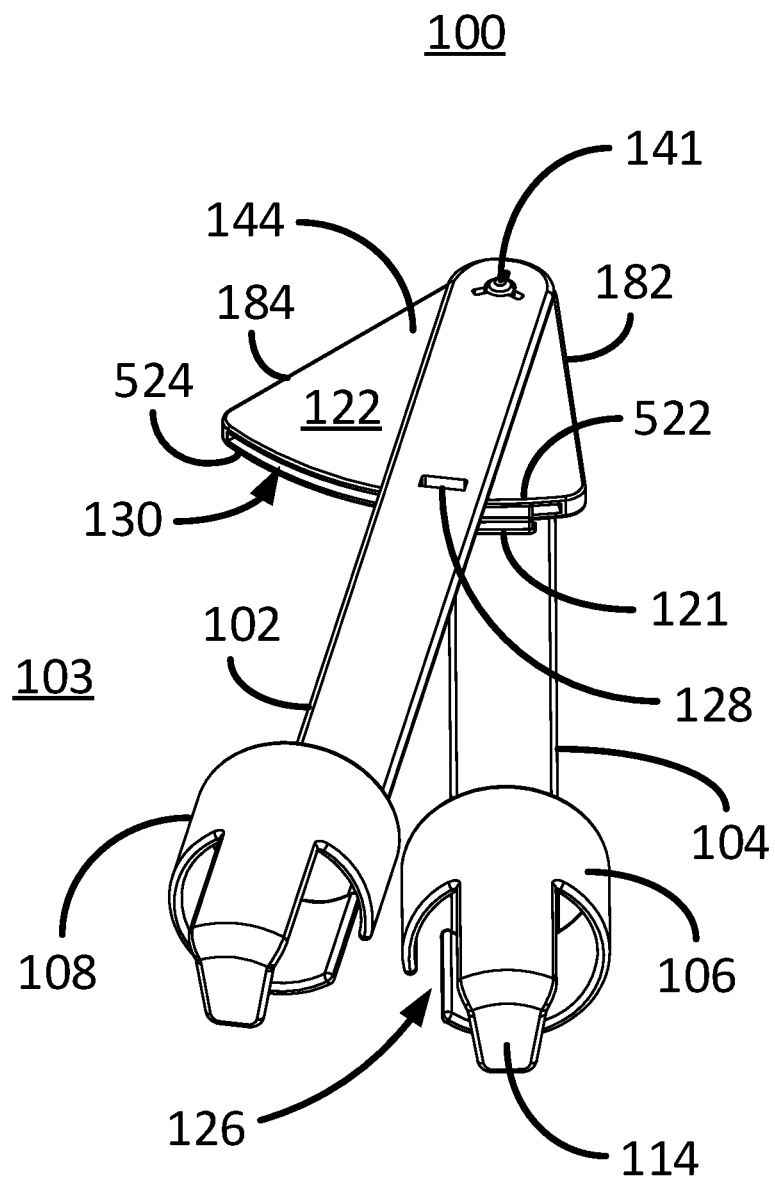

FIG. 1E illustratively depicts a line drawing of a top perspective view of the caliper back side 103 finger caliper embodiment 100 (view of the back side 103 of the finger calipers 100) whereby the index finger retention tab 121 is engaged with the palm plate slot 130, as shown. As should be appreciated, the index finger retention tab 121 and the second finger retention tab 128 are slidingly engaged with the palm plate slot 130 and are constrained between the palm plate leading edge 182 and the palm plate trailing edge 184. Accordingly, the lever arms 102 and 104 cannot be made to move outside of the limits defined by the palm plate leading edge 182 and trailing edge 184.

Figure 2:
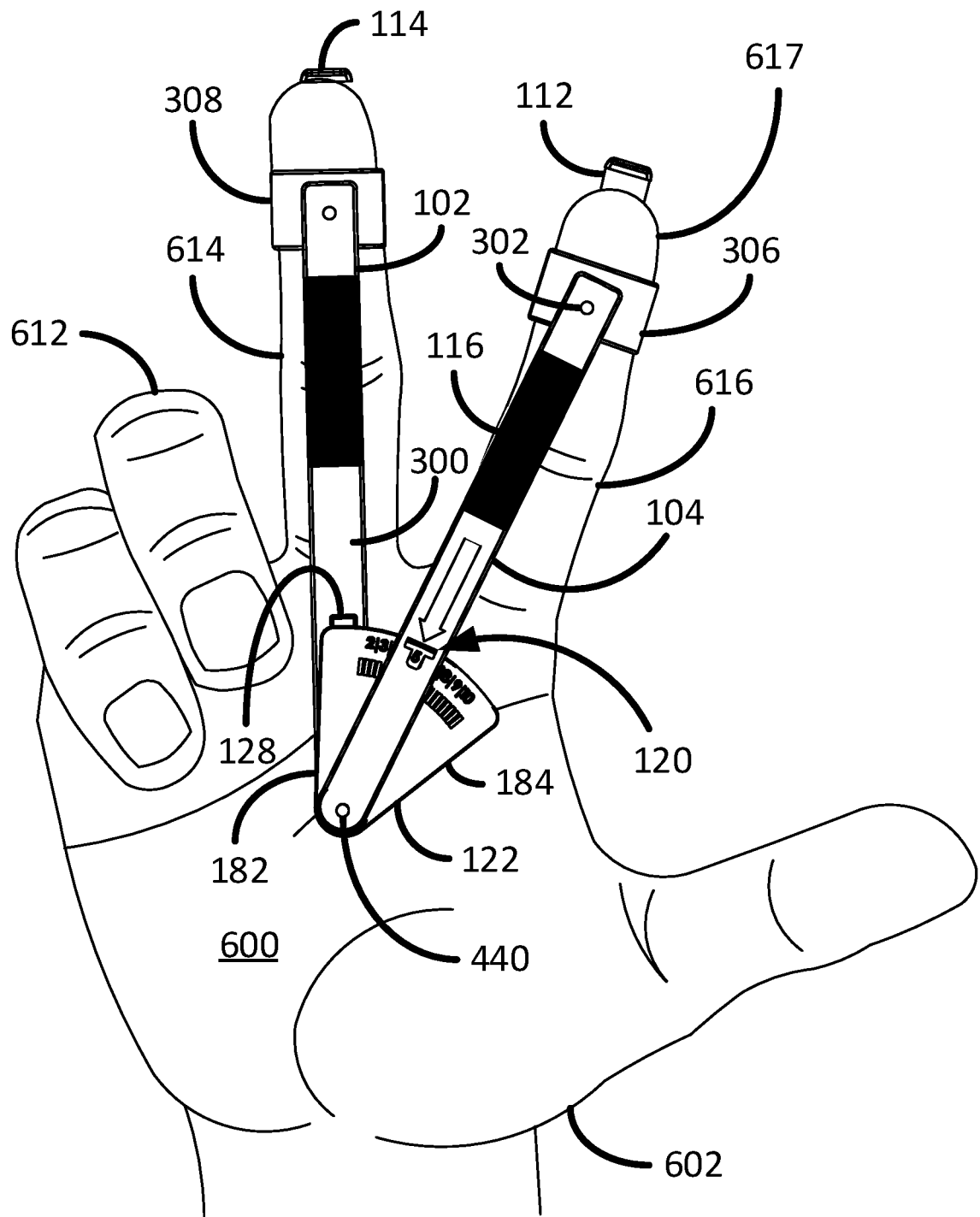
FIG. 2 illustratively depicts a line drawing of finger calipers embodiment 300 engaged with a human hand consistent with embodiments of the present invention.

FIG. 2 illustratively depicts a line drawing of a finger caliper embodiment 300 engaged with a human hand consistent with embodiments of the present invention. As shown, the finger calipers 300 (and more specifically the palm plate 122) are positioned over the human palm 600 of a human hand 602 with the index finger cuff 306 and the second finger cuff 308 at least partially wrapped around fingers 610 and 614, respectively. The finger calipers embodiment 300 is similar to the finger calipers embodiment 100, of FIG. 1A-1E, however the finger cuffs 306 and 308 can pivot about cuff pivot points 302 in order to accommodate positioning of the fingers 616 and 614. In the present embodiment, the graduated palm plate 122 free floats over the human palm 600. The index finger lever arm 104 extends along the human index finger 616 and attaches to the index finger distal phalange 617 via the first finger cuff 306. Certain embodiments envision the first finger cuff 306 attaching between the index finger distal phalange 617 and the second phalange around the finger knuckle if the hand 602 is particularly small. In this present depiction, the second finger lever arm 102 extends along the middle finger 614. However, to accommodate sufficiently spreading fingers on a smaller hand 602 in order to measure a dilated cervix, the second finger lever arm 102 can just as easily extend along and attach to the ring finger 612. As shown here, one of the fingertip caps 114 is resting atop the fingertip of the middle finger 614, however the other fingertip cap 114 from the index fingertip extender 112 is not in contact with the index fingertip. In this embodiment, the index fingertip extender 112 is the same length as the second fingertip extender 110 (shown in FIG. 1A) essentially providing equal length arms of a triangle to accurately translate measurement of the cervix to the indicia 125. In the present depiction, the index finger 616 and the middle finger 614 are spread 5 cm apart. Accordingly, when the index finger 616 and the middle finger 614 are spread apart to contact the edge/rim of a cervix that is dilated 5 cm, the graduated palm plate reads 5 cm though the window 120. Certain embodiments envision the finger calipers 300 being covered by a surgical glove along with the hand 602. As shown, the index finger lever arm 104 and said second finger lever arm 102 splay/spread apart like scissors. To splay is intended to mean spread out and apart, as in the ends 114A and 114B of the calipers 300 when the fingers are spread apart. Embodiments of the present invention envision the finger calipers 300 being put on a medical practitioner's hand and then covered with a glove. In this way, the calipers 300 and hand 602 are hermetically covered inside of a surgical (e.g., latex) glove preventing contamination between the device and woman or vise versa. Moreover, any sharp edges are protected from coming into direct contact with a woman. Other embodiments envision the calipers 300 being discarded after use.

Figure 3:
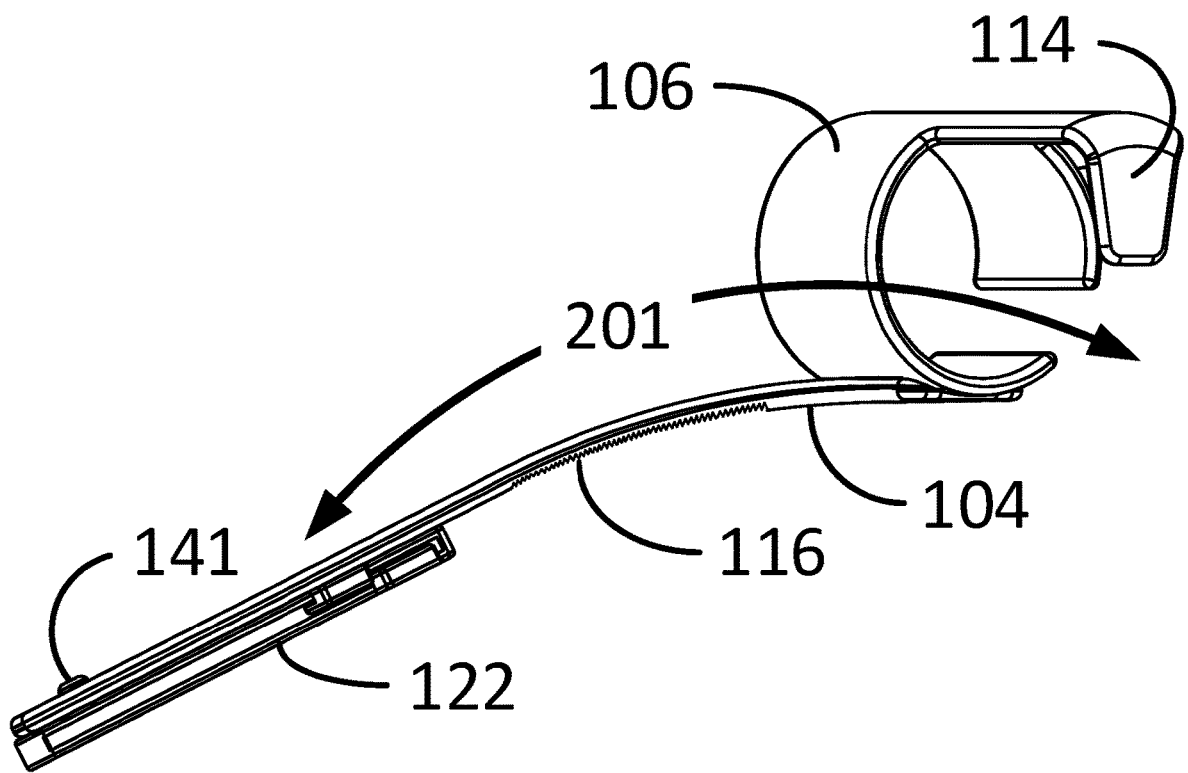
FIG. 3 illustratively depicts a line drawing side view of the index finger lever arm 104 bent to accommodate the natural movement of a finger consistent with embodiments of the present invention.

FIG. 3 illustratively depicts a line drawing side view of the index finger lever arm 104 bent to accommodate the natural movement of a finger consistent with embodiments of the present invention. As shown, the index finger lever arm 104 is bent along the arc indicated by double arrow 201. The finger bending grooves 116 provide improved deflection of the lever arms 102 and 104 to accommodate the natural movement of curling fingers 612, 614, 616 (FIG. 2). Certain embodiments envision the lever arms 102 and 104 made from a flexible material such as PVC, for example.

Figure 4A:
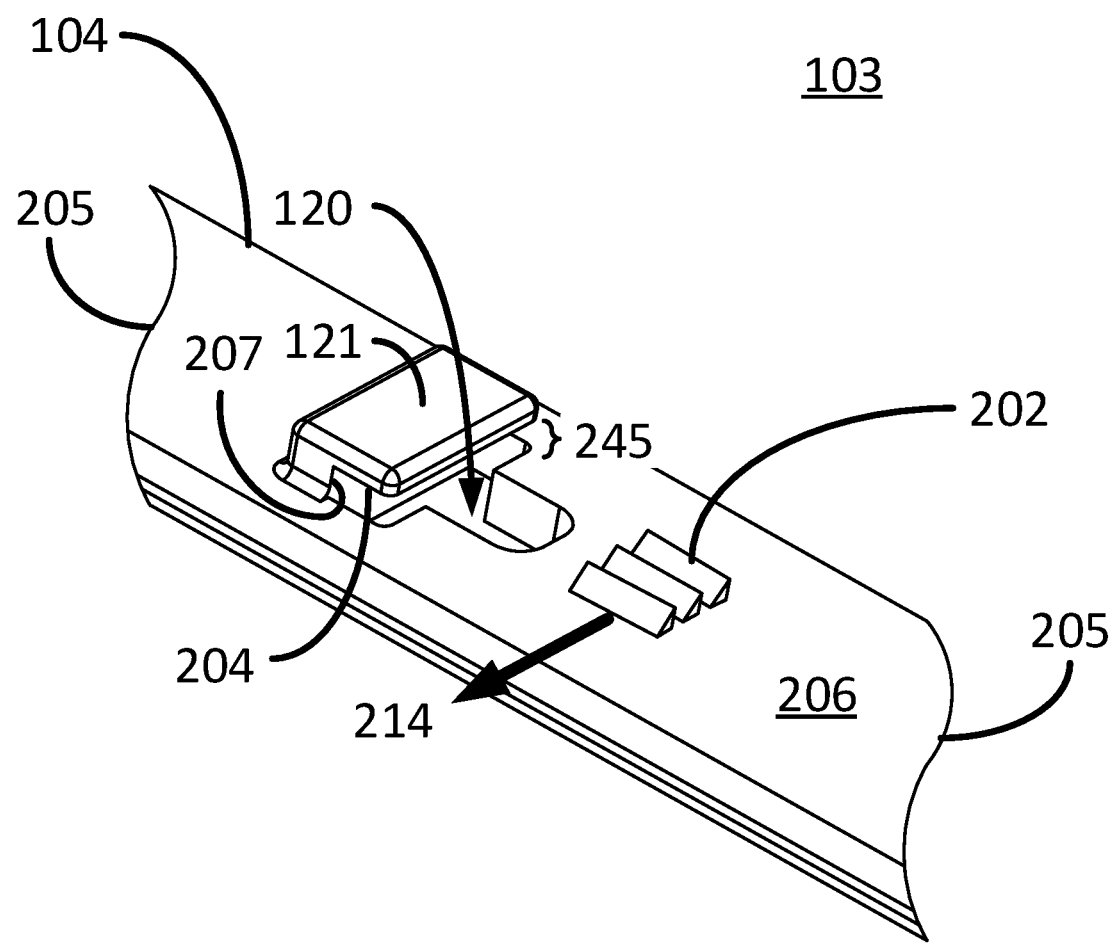
FIG. 4A illustratively depicts an isometric section line drawing view of a male portion of a ratchet system on the index finger lever arm consistent with embodiments of the present invention.

FIG. 4A illustratively depicts an isometric section line drawing view of the male portion of a ratchet system comprised by the index finger lever arm 104 consistent with embodiments of the present invention. In this illustration, a section of the index finger lever arm 104 is shown between the section lines 205. The index finger retention tab 121 extends from the index finger lever arm backside 206 (as viewed from the calipers' backside 103) and further comprises a retention tab lip 204 (lipped bracket structure) that points towards the pivot point 440. As shown, a slotted channel 245 is created between the index finger lever arm backside surface 206 and the retention tab lip 204. The retention tab lip 204 slidingly captures/engages the front top edge 522 (FIG. 1E) of the graduated hand plate 122 to hold the index finger lever arm 104 on the palm plate 122. In other words, the retention tab channel 245 in a slidingly engaged relationship captures the palm plate front top edge 522. Slidingly captures is intended to mean that the retention tab lip 204 is inside the palm plate slot 130 and the front top edge 522 of the graduated hand plate 122 butts up against, or is in close proximity, to the inner back edge 207 of the index finger retention tab lip 204. Hence, the index finger retention tab 121 retains the index finger lever arm 104 to the front top edge 522 of the graduated hand plate 122 and holds the male ratchet features 202 in contact with the plurality of slots 115 (FIG. 1A), which comprise the female component of the ratchet system 115. The index finger retention tab lip 204 further constrains the index finger lever arm 104 between the graduated palm plate leading edge 184 and the graduated palm plate trailing edge 182. Also shown here are three male ratchet features 202, which extend outwardly from index finger lever arm backside 206.

Figure 4B:
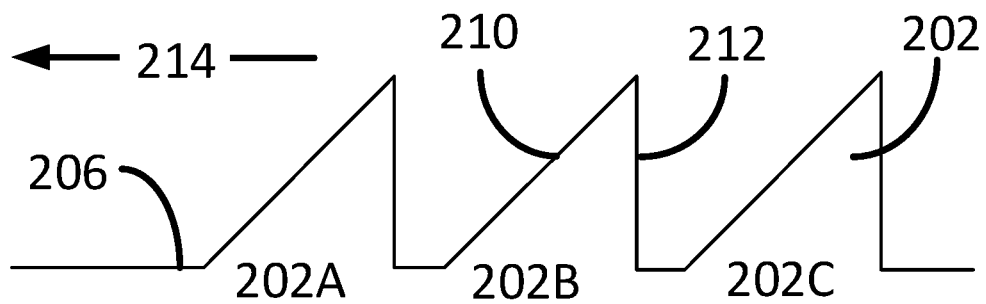
FIG. 4B illustratively depicts a side view line drawing of the male ratchet features consistent with embodiments of the present invention.

FIG. 4B illustratively depicts a side view line drawing of the male ratchet features 202 consistent with embodiments of the present invention. The male ratchet features comprise three angled wedges 202A, 202B and 202C that have a sloped leading edge 210 and right angle trailing edges 212 relative to the index finger lever arm back side surface 206. The sloped leading edges 210 and the right angle trailing edges 212 allow movement only in the direction of the arrow 214. Other embodiments contemplate fewer or more angled wedges 202. Yet other embodiments envision cylindrical shaped male features, pins, or other male structures that would be understood by those skilled in the art after the benefit of understanding the present disclosure.

Figure 4C:
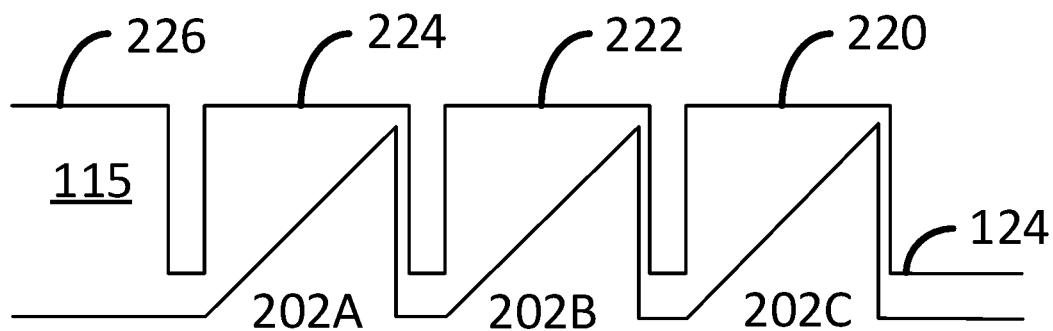
FIGS. 4C-4E illustratively depict side view line drawings of the male ratchet feature engaging the female ratchet feature consistent with embodiments of the present invention.
Figure 4D:
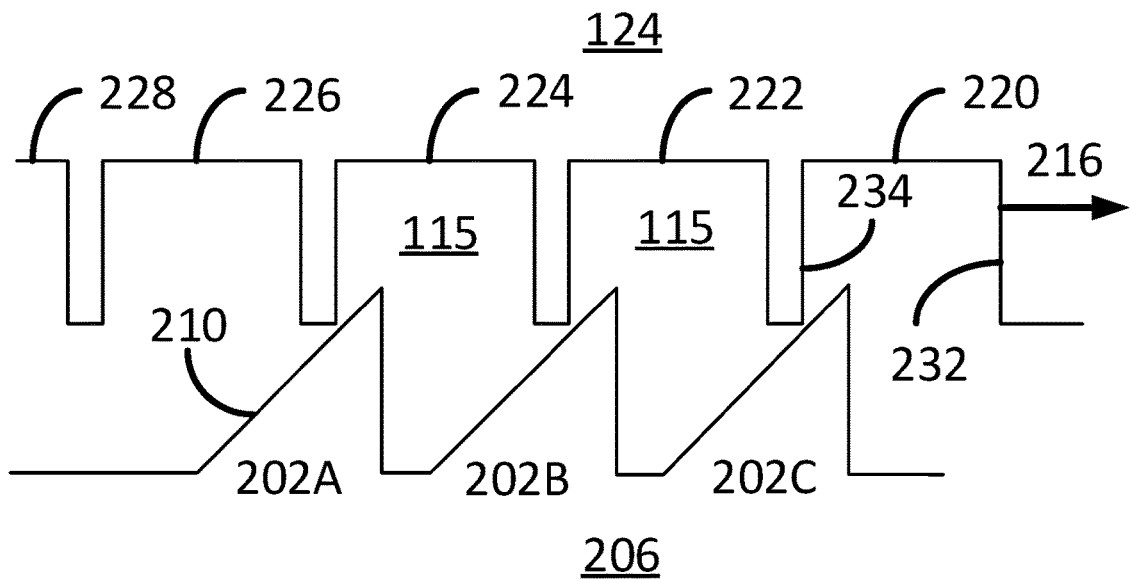
Figure 4E:
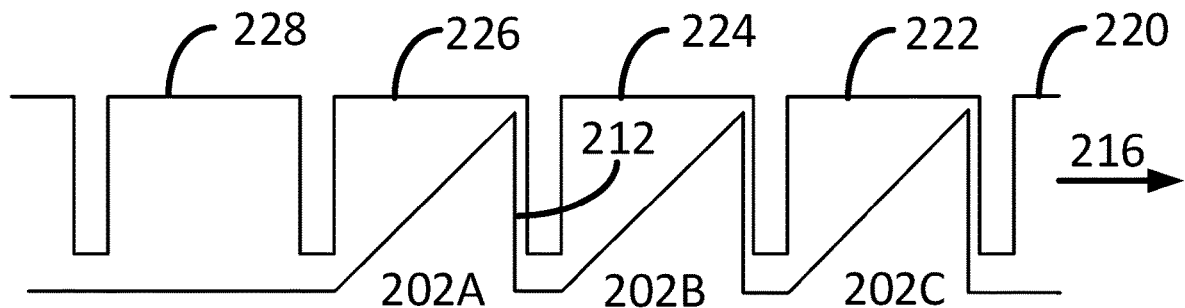

FIGS. 4C-4E illustratively depict a side view line drawings of the male ratchet feature 202 cooperating with the female ratchet feature 115 consistent with embodiments of the present invention. In FIG. 4C, the index finger lever arm 104 is in the starting position over the graduated hand plate 122, which corresponds to "0" or the lowest indicium (setting/value) 125 viewable through the window 120. Accordingly, the male ratchet features 202 are engaged with the female features 115 that are to the far left in FIG. 1A. More specifically, the wedges 202A, 202B and 202C are inside slots 224, 222 and 220, respectively. As indicated here, the plurality of female slots 115 extend inwardly from the graduated palm plate front surface 124.

FIG. 4D illustratively depicts the index finger lever arm 104 moving in one direction over the graduated palm plate 122 because the slots can only move relative to the wedges 202 in the direction of the arrow 216. The leading wedge edges 210 slide along the leading slot edges 234, which causes the front palm plate surface 124 to move away from the index finger lever arm backside surface 206, as shown. This is accomplished by deflecting either the index finger lever arm 104 (FIG. 1A), the graduated palm plate 122 (FIG. 1A), or both (while the index finger lever arm 104 is attached to the graduated palm plate 122 in two places, i.e., via the pivot point 440 and the retention tab 121). Accordingly, certain embodiments envision the index finger lever arm 104 and/or the graduated palm plate 122 being made out of PVC, metal, or some other material that can accommodate the spring loaded deflection. Because the index finger lever arm 104 must deflect away from the graduated palm plate 122, there is an additional force resisting movement of the index finger lever arm 104 in an arced path over the graduated palm plate 122 (see the arced layout of the slots 115 in FIG. 1A). In other words, there is a small resisting force to spread apart the human fingers attached to the cervix dilation calipers 100.

FIG. 4E illustratively depicts the index finger lever arm 104 ratcheting into position against the graduated palm plate 122. Because the index finger lever arm 104 is deflecting away from the graduated palm plate 122 during the step of FIG. 4D, once the wedges 202 are in place over the next set of slots 115, the male 202 and female 115 ratchet components snap into place. Accordingly, wedge 202A is now moved into slot 226, wedge 202B it is now moved into slot 224, and wedge 202C is now moved into slot 222. As discussed, this ratchet system 115 and 202 can only move in one direction because the trailing wedge edge 212 locks against (i.e., lockingly engages) the trailing slot edge 232. As the wedges 202, such as wedge 202A, moves from slot 224 to slot 228, and so forth, the index finger lever arm 104 moves unidirectional across the graduated palm plate 122 thereby reflecting how much the index finger 616 has spread relative to the second finger 614 when measuring a dilated cervix.

Figures 5A, 5B:
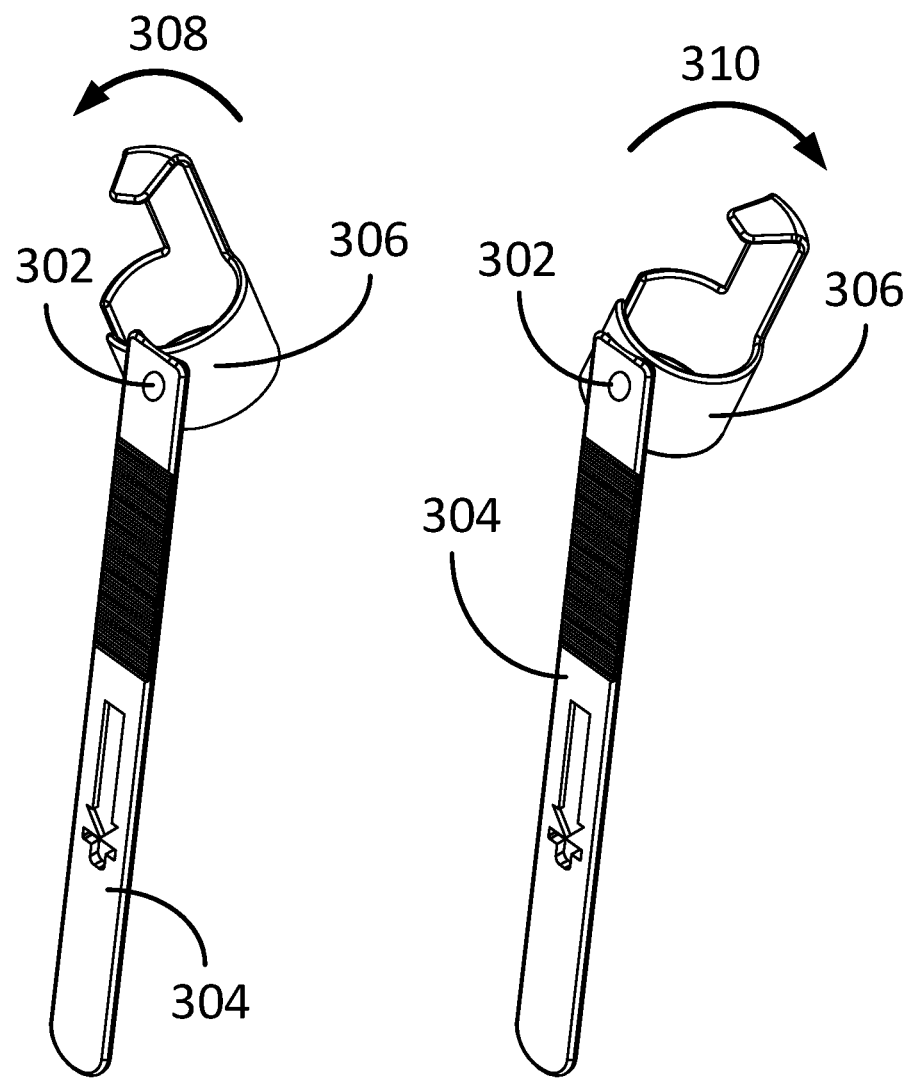
FIGS. 5A and 5B illustratively depict line drawings of an alternative embodiment of a finger lever arm consistent with embodiments of the present invention.

FIGS. 5A and 5B illustratively depict line drawings of an alternative finger lever arm embodiment consistent with embodiments of the present invention. The index finger lever arm arrangement 320 is similar to the index finger lever arm 104 previously described but differs in that the finger cuff 306 can pivot about pivot point 302. Here, the index finger lever arm 304 is connected to the finger cuff 306 by way of a pin 302. Accordingly, the finger cuff 306 can pivot to the left 308 or to the right 310. In this way, the finger cuff 308 can accommodate movement of the human finger as it spreads apart from a second finger. Furthermore, the pivoting finger cuff 308 can accommodate a crooked finger. The pivoting finger cuff 308 depicted in this index finger lever arm arrangement 320 is envisioned to be equally used with a second finger lever arm 312, shown in FIG. 6.

Figure 6:
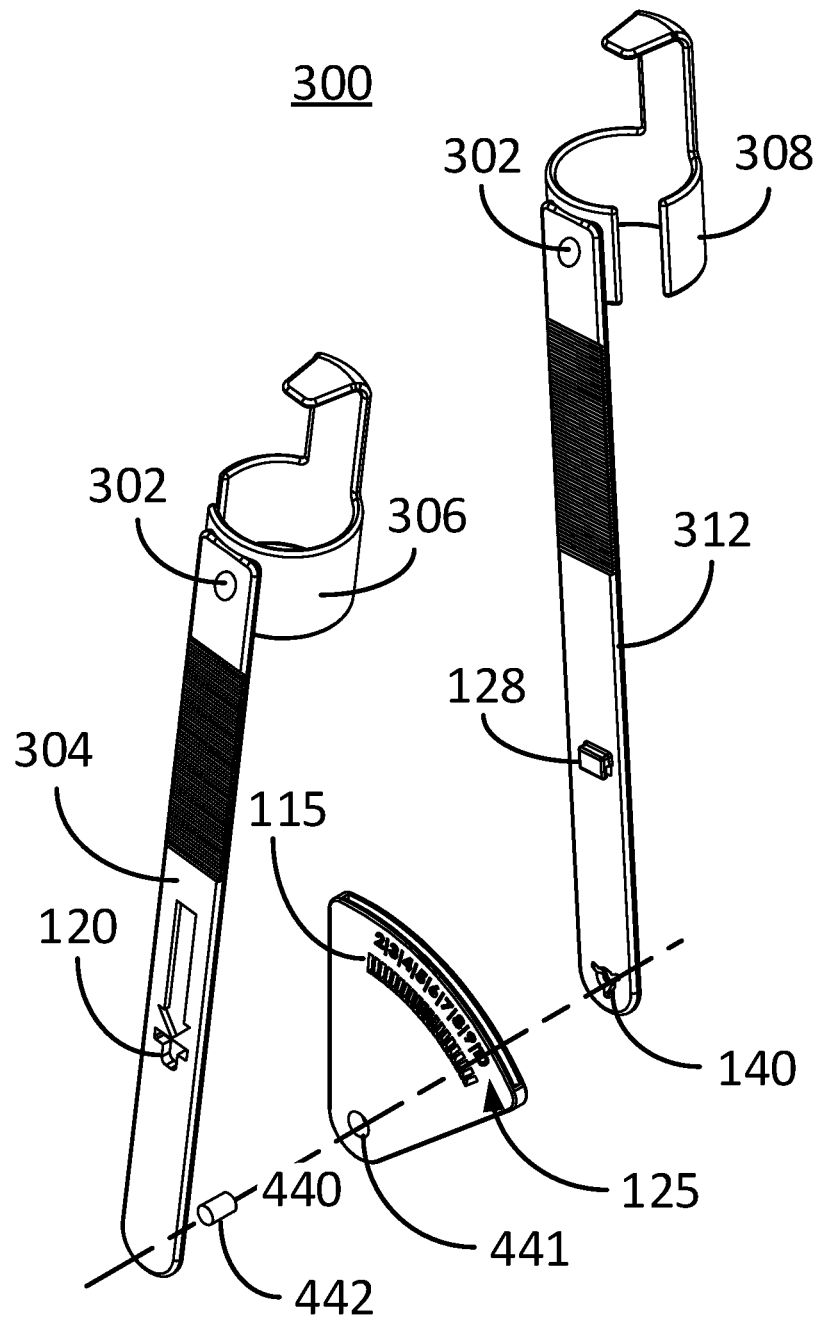
FIG. 6 illustratively depicts an exploded view line drawing of finger calipers embodiment consistent with embodiments of the present invention.

FIG. 6 illustratively depicts an exploded view line drawing of a finger calipers embodiment consistent with embodiments of the present invention. A person, skilled in the art, will appreciate that this exploded view of the finger caliper 300 can be equally applied to the finger calipers embodiment 100 without departing from the scope and spirit of the present invention. The exploded view line drawing depicts the index finger lever arm 304 connecting to the second finger lever arm 312 by way of a pin 442 on the back side 206 of the index finger lever arm 304. The present embodiment envisions a pin 442 extending at the pivot point line 440 orthogonally from the back side 206 (FIG. 4A) of the index finger lever arm 304 passing through a palm plate hole 441 in the bottom of the palm plate 122 and into a snap-hole (lock ring) 141 in the second finger lever arm 312. The pin 442 facilitates anchoring the index finger lever arm 304 to the second finger lever arm 312 allowing them to pivot freely about the pivot point 440.

Figure 7A:
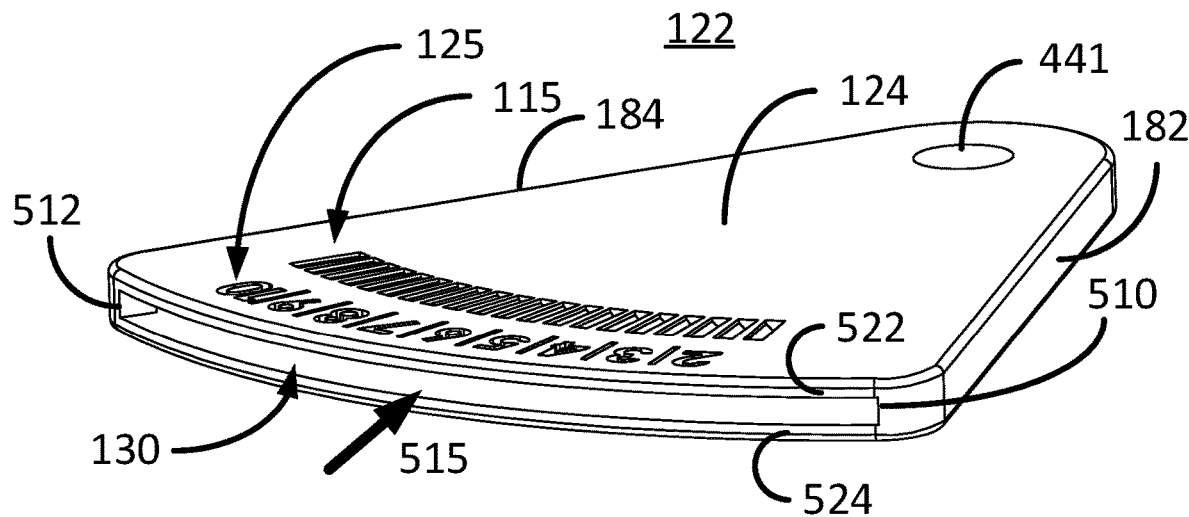
FIG. 7A illustratively depicts an isometric top view line drawing of a palm plate consistent with embodiments of the present invention.

FIG. 7A illustratively depicts an isometric top view line drawing of a palm plate consistent with embodiments of the present invention. The front surface side 124 of the graduated palm plate 122 identifies a first lever arm stop 510 and a second lever arm stop 512. The palm plate slot 130 is defined as framed by the front top edge 522, the back top edge 524 and the lever arm stops 510 and 512.

Figure 7B:
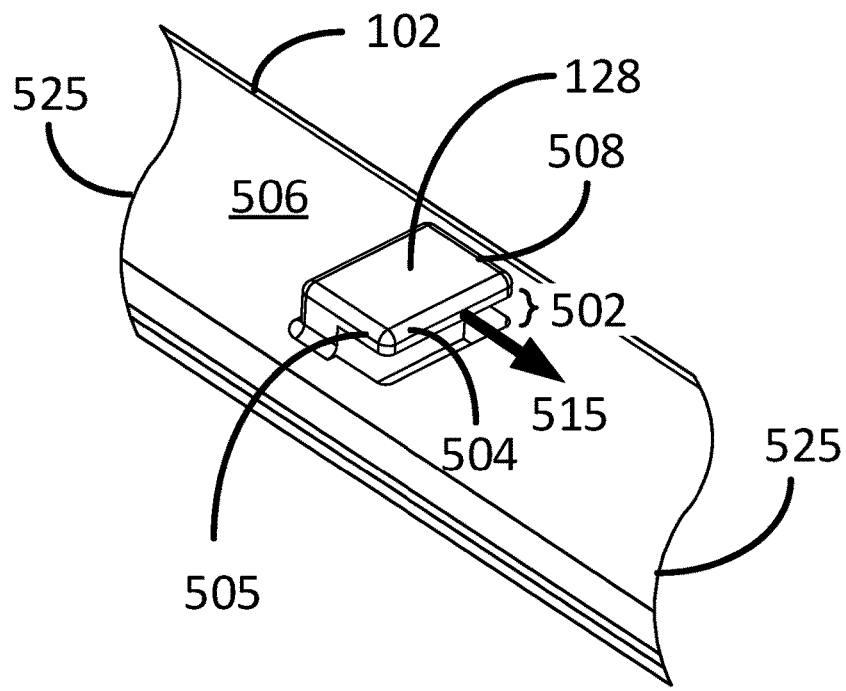
FIG. 7B illustratively depicts a portion of the second finger lever arm with the second finger retention tab shown between section lines consistent with embodiments of the present invention.

FIG. 7B illustratively depicts the second finger retention tab 128 in a section of the second finger lever arm 102 shown between section lines 525 consistent with embodiments of the present invention. The second finger retention tab 128 has a retention tab lip 504 which is essentially a lipped bracket that fits inside the palm plate slot 130, as shown by arrow 515. As further shown, the second finger retention tab 128 extends in an outward direction from the second finger lever arm front side 506 (that is, as viewed from the front side 101 of the finger calipers 100). A portion/lip of the back top edge 524 is slidingly engaged in the retention tab channel 502 (the palm plate back top edge 524 is captured by the retention tab channel 502). The retention tab 128 constrains the second finger lever arm 102 between the palm plate leading edge 182 and the palm plate trailing edge 184 when engaged with the palm plate slot 130. That is, the retention tab trailing edge 505 contacts the first lever arm stop 510 when closest to the palm plate leading edge 182 and the retention tab leading edge 508 contacts the second lever arm stop 512 when closest to the palm plate trailing edge 184.

Figure 7C:
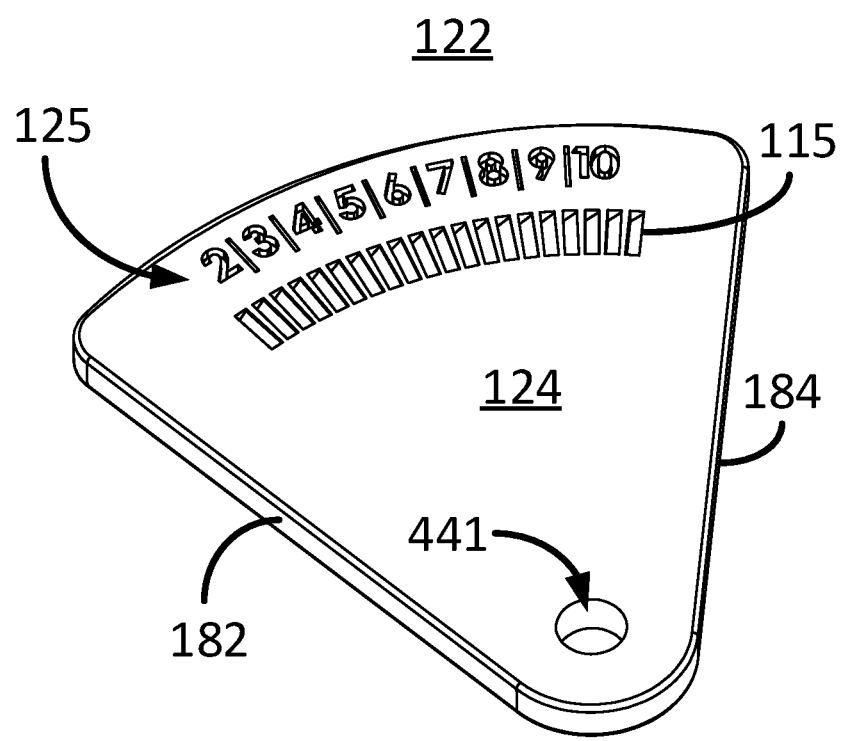
FIG. 7C illustratively depicts a line drawing of the graduated palm plate consistent with embodiments of the present invention.

FIG. 7C illustratively depicts a line drawing of the graduated palm plate 124 consistent with embodiments of the present invention. The graduated palm plate 124 simply depicts a high-resolution illustration showing the palm plate leading edge 182 and the palm plate trailing edge 184, the palm plate hole 441, the graduated indicia 125 (representing measurements which increase 1 cm at a time up to 10 cm), and the ratchet slots 115.

Figure 8A:
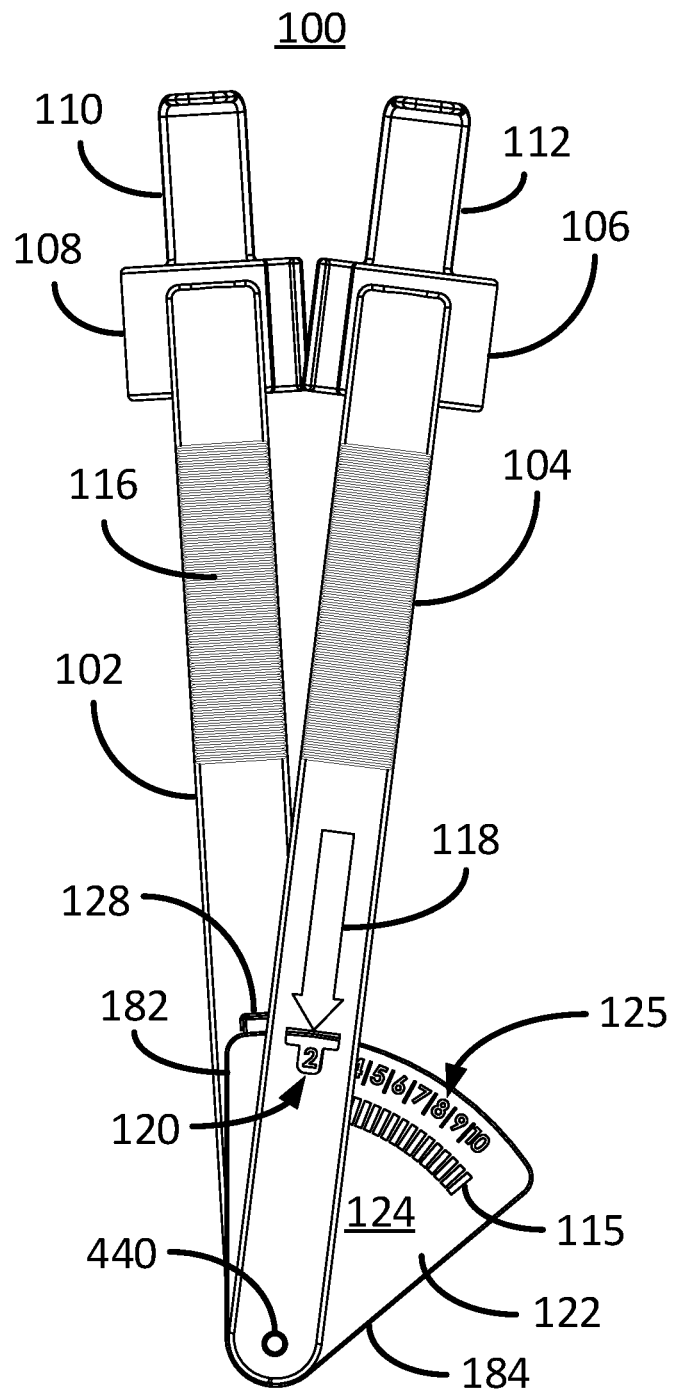
FIGS. 8A-8C illustratively depict line drawings of the cervix dilation calipers in operation consistent with embodiments of the present invention.
Figure 8B:
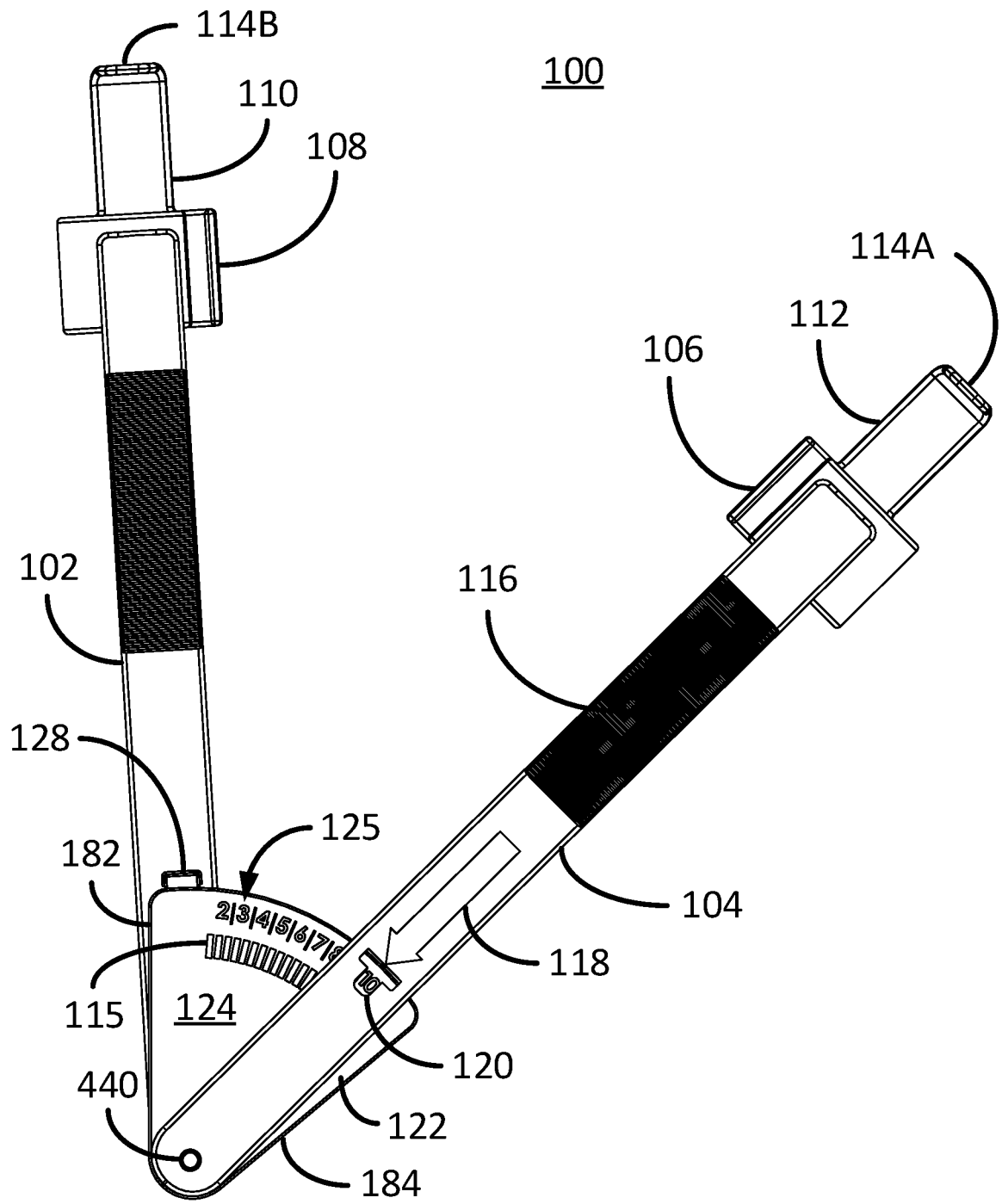
Figure 8C:
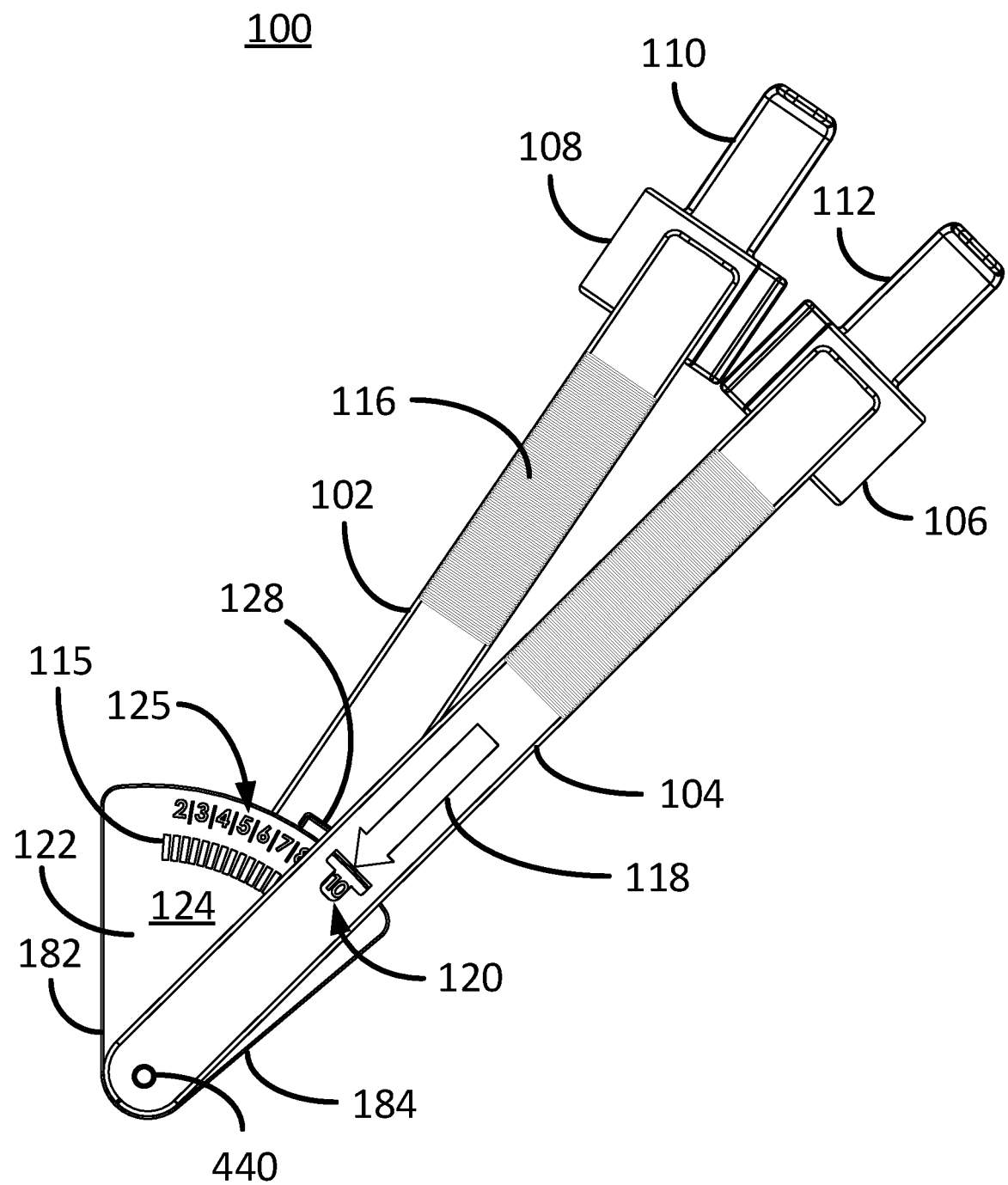
Figure 9:
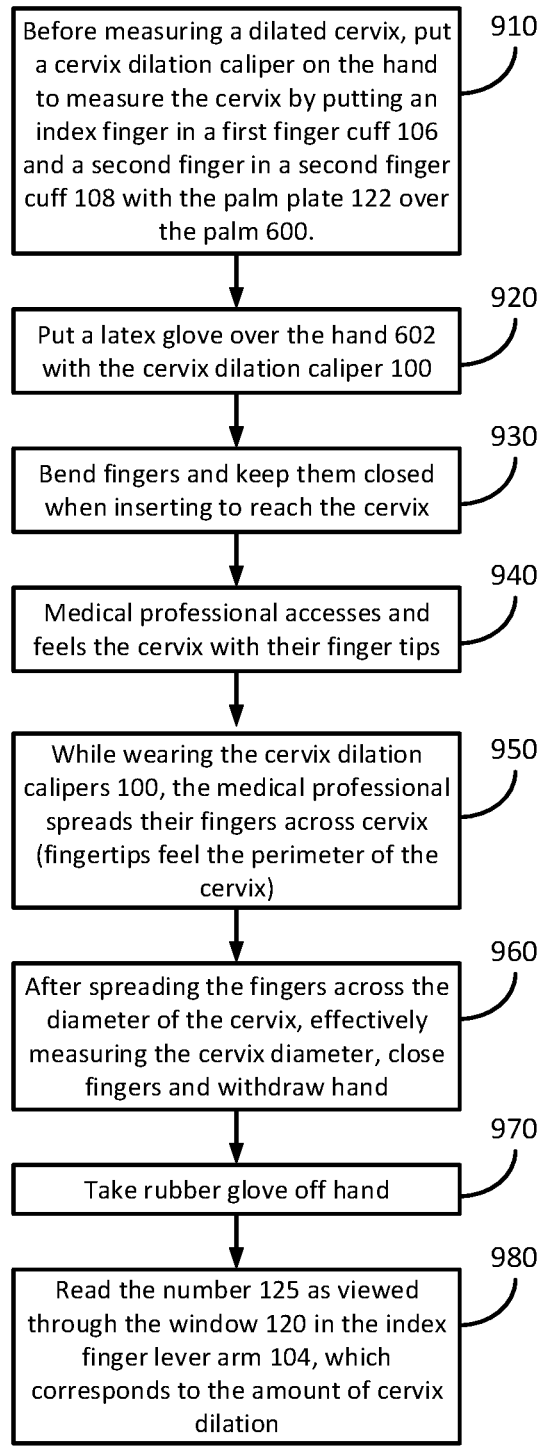
FIG. 9 is a block diagram of a method to use calipers embodiment consistent with embodiments of the present invention.

FIGS. 8A-8C illustratively depict line drawings of the cervix dilation calipers 100 in operation consistent with embodiments of the present invention. FIGS. 8A-8C are described in view of FIG. 9, which is a block diagram of a method to use a caliper embodiment, such as calipers 100 or 300. The primary method used to evaluate how far along a woman is in labor is to determine the diameter of her dilated cervix. In one embodiment, a medical professional slides their index finger 616 into the first finger cuff 106 (or optionally 306 when using the caliper 300) and the second finger cuff 108 with the palm plate 122 hovering over the medical professionals palm 600, step 910. FIG. 8A shows a starting position of the calipers 100 when the cervix dilation is equal to or less than 2 cm, as shown through the window 120. The medical professional can freely slide on a latex glove, step 920. Because the index finger lever arm 104 and the second finger lever arm 102 have the finger bending grooves 116, the medical professional can naturally bend their fingers when accessing the dilated cervix, step 930. When the medical professional has accessed the dilated cervix, step 940, medical professional simply spreads their fingers across the dilated cervix, step 950. By spreading their fingers, the index finger lever arm 104 and the second finger lever arm 102 spread apart in a scissor like manner at the pinned together pivot point 440. By spreading their fingers, the second finger lever arm retention tab 128 is forced to butt up against (presses against) the first lever arm stop 510 while the index finger lever arm 104 ratchets across the graduated palm plate 122. As shown in FIG. 8B, the tip 114A of the index finger lever arm is 10 cm apart from the tip 114B of the second finger lever arm 102, which registers '10' viewably displayed in the window 120 indicating 10 cm. Once the medical professional has adequately felt the dilated cervix by spreading their index finger 616 and second finger 614 apart, the medical professional can bring the two fingers 616 and 614 together to retract their hand 602 from the dilated cervix, step 960. When the medical professionals fingers close in step 960, the second finger lever arm 102 freely moves to meet the index finger lever arm 104, which is locked in place relative to the graduated palm plate 122 as shown in FIG. 8C. In this way, the medical professional can move their fingers after the measurement is taken without altering the dilated cervix measurement (assuming the medical professional does not spread their fingers apart wider than that of the measurement taken). After pulling their hand 602 away from the cervix, the medical professional need only slide off the rubber glove, step 970, and read the number 125 inside of the window 120 to determine the diameter of the dilated cervix, step 980. Because the palm plate 122 can float over the medical examiner's palm 600 (either high on the palm 600 or low on the palm 600 near the wrist), consistent cervical measurements can be taken no matter how large or small the hand 602. Certain other embodiments envision a see-through glove allowing the medical professional to see the amount of cervical dilation without taking the glove off.

Figure 10A:
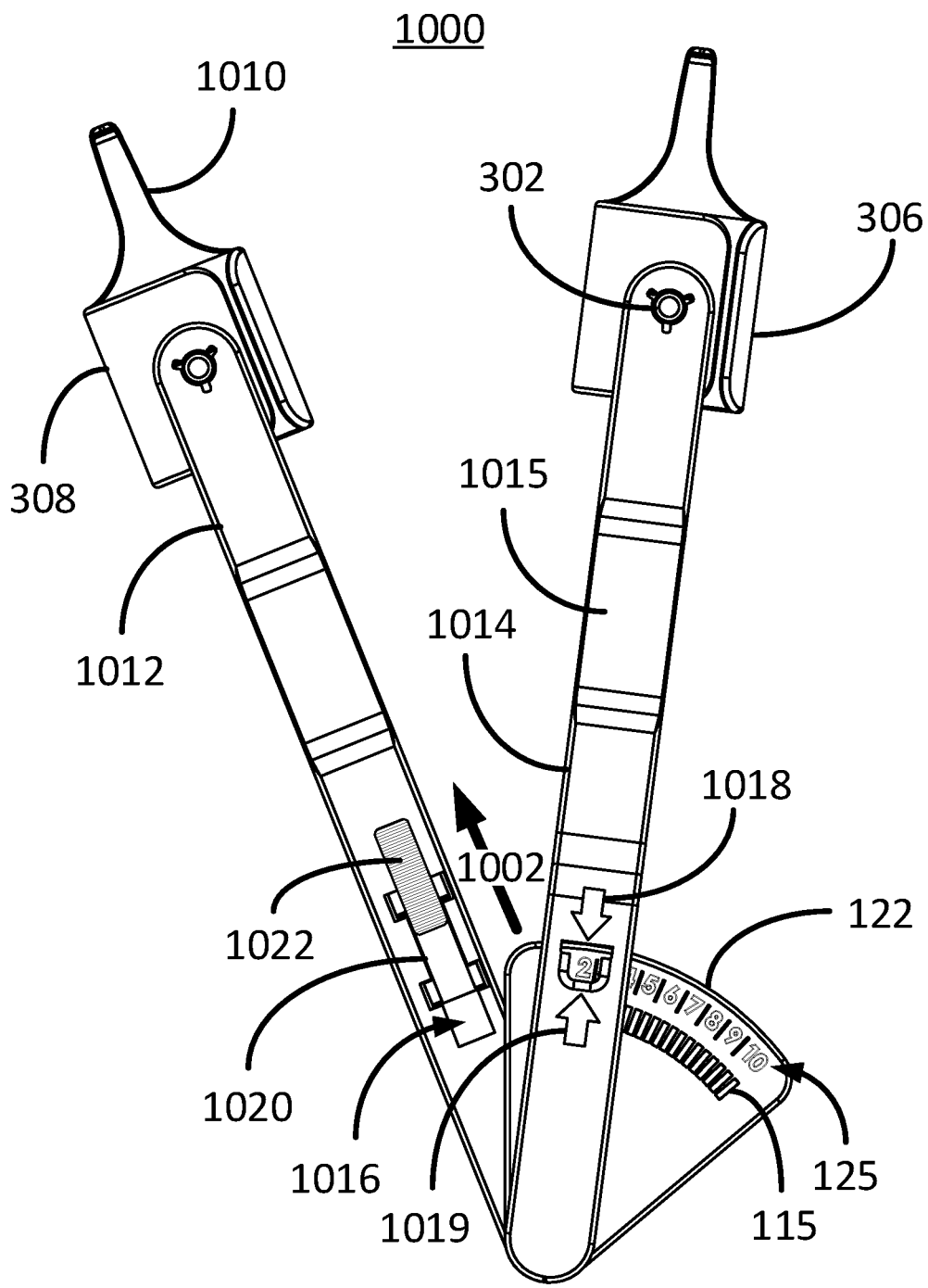
FIGS. 10A and 10B are line drawings of a locking finger caliper embodiment as viewed when looking at the palm of a human hand.
Figure 10B:
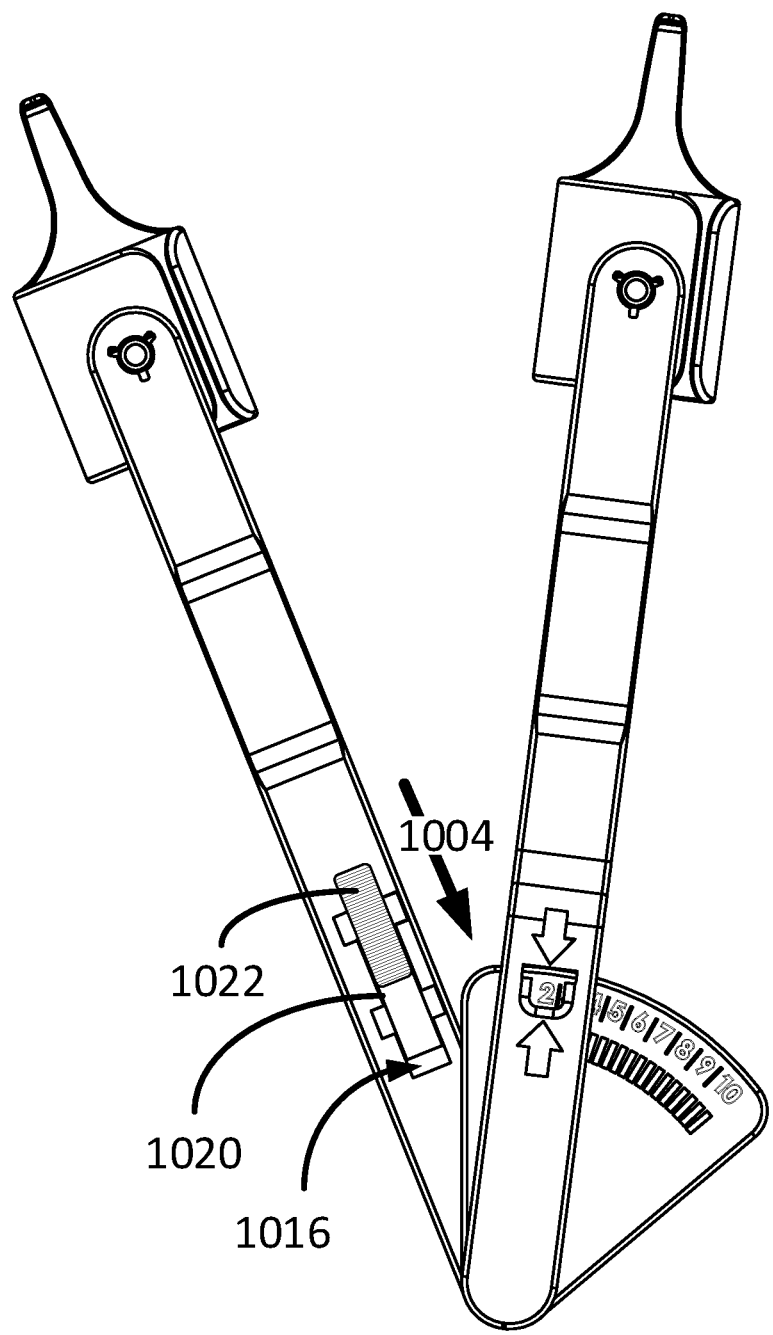
Figure 11:
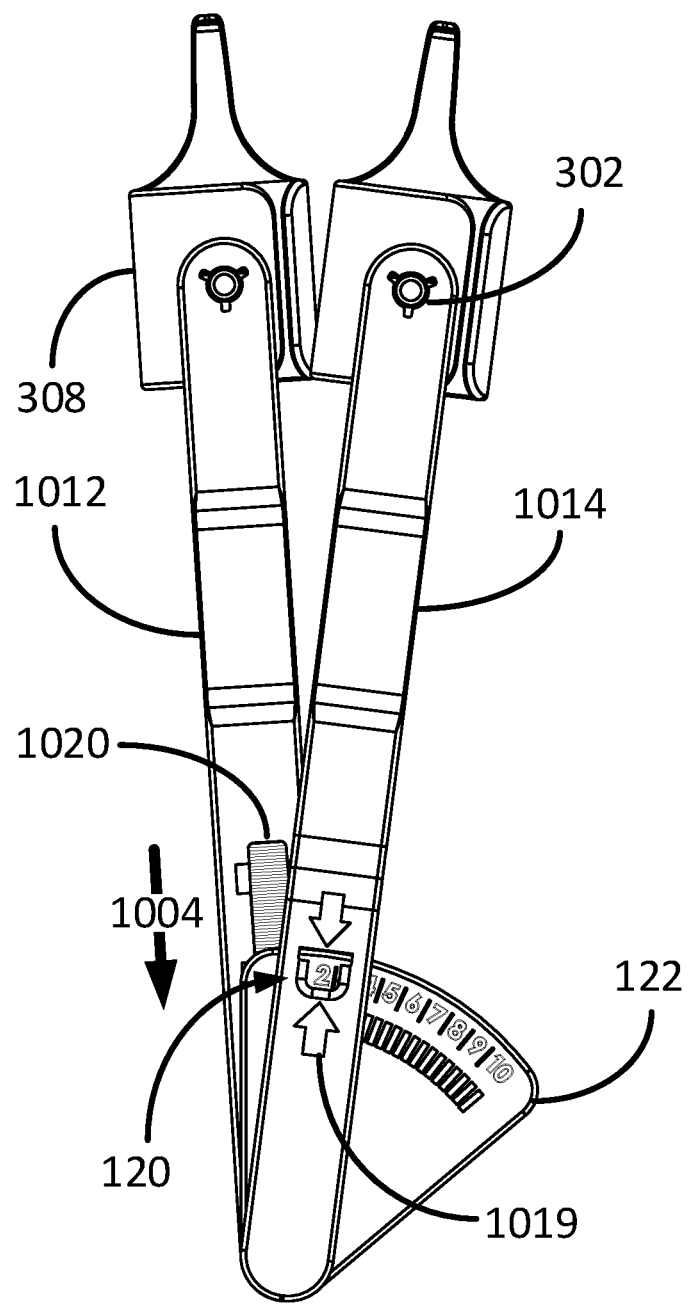
FIG. 11 illustratively shows a line drawing of the finger caliper embodiment with the second finger lever arm engaged over the palm plate in a normally assembled configuration.

FIGS. 10A and 10B are line drawings of a locking finger caliper embodiment 1000 as viewed when looking at the palm 600 of a human hand 602. FIG. 10A is similar to the other finger caliper embodiments described to this point except that finger calipers 1000 comprise thinner fingertip extenders 1010, a thin finger bending region 1015, a pair of dilation measurement arrows 1018 and 1019, and a locking slider 1020. The locking slider 1020 incorporates an embodiment of the second finger retention tab 1504 (see FIG. 13C) with a sliding retention tab 1045 that slides back and forth in a locking slot 1016. The present locking slider 1020 includes finger-gripping grooves 1022 to better assist an operator in sliding the locking mechanism 1020 in different positions (1002 and 1004). FIGS. 10A and 10B depict the second finger lever arm 1012 in a pre-assembly orientation to improve viewing the locking mechanism 1020 in operation, i.e., the second finger lever arm 1012 is not engaged over the palm plate 122. Unlike FIGS. 10A and 10B, in normal operation the second finger lever arm 1012 is engaged with the palm plate 322, as depicted in FIG. 11. In FIG. 10A, the locking slider 1020 is in a non-engaged (upward located) position in the locking slot 1016 as shown by the upward facing arrow 1002. As shown in FIG. 10B, the locking slider 1020 is pushed downward in a locking/engaged (downward located) position in the locking slot 1016 as indicated by the downward facing arrow 1004.

FIG. 11 illustratively shows a line drawing of the finger caliper embodiment 1000 with the second finger lever arm 1012 engaged over the palm plate 122 in a normally assembled configuration. As shown, the locking slider 1020 is engaged with the palm plate 122, and more specifically with the palm plate slot 130 as indicated by the arrow 1004.

Figure 12:
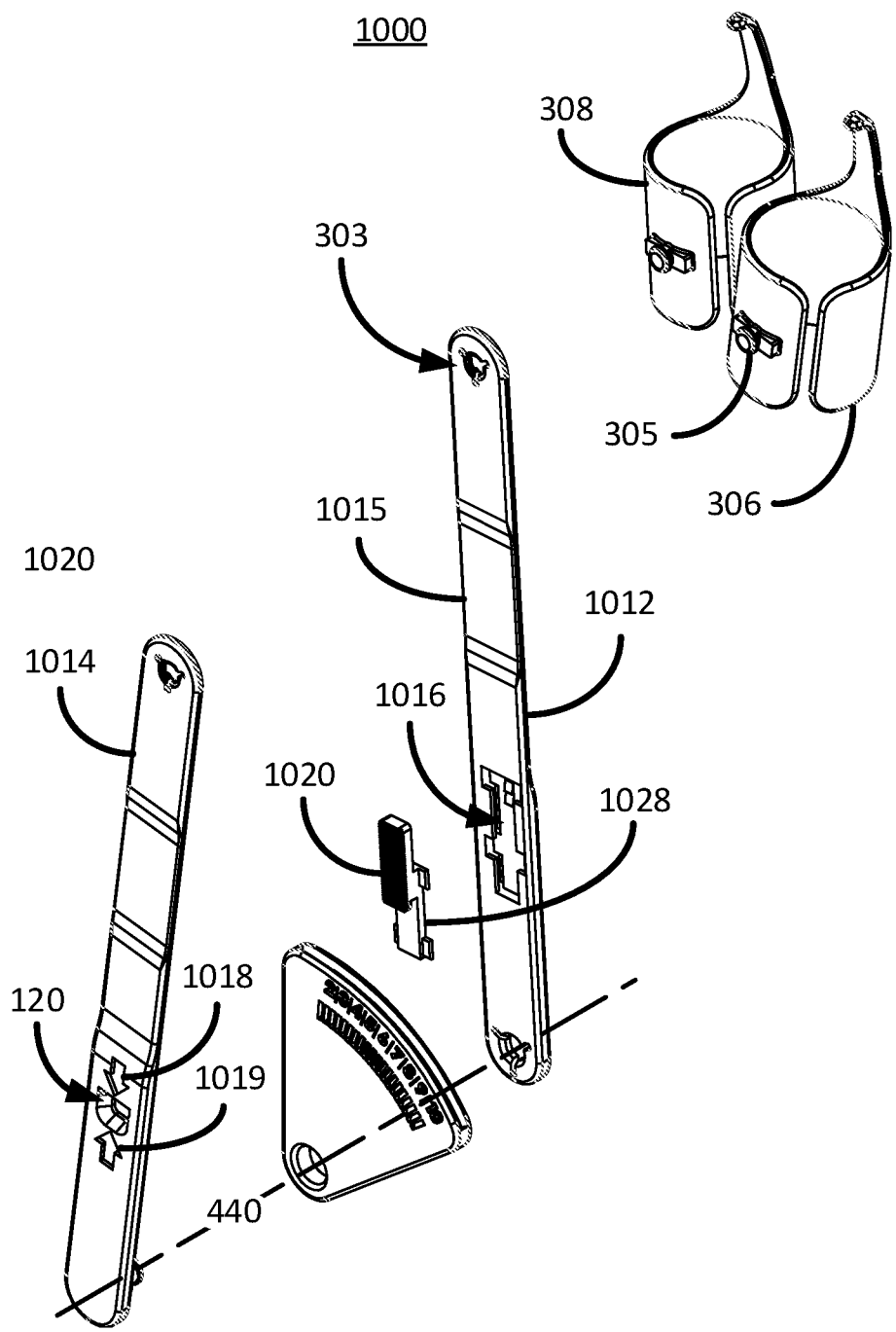
FIG. 12 depicts an exploded view line drawing of the finger caliper embodiment within the scope and spirit of the present invention.

FIG. 12 depicts an exploded view line drawing of the finger caliper embodiment 1000 within the scope and spirit of the present invention. The index finger cuff 306 and the second finger cuff 308 illustratively show the pivot pins 305 that connect to a corresponding receiving pivot aperture 303. The pivot pins 305 and the pivot apertures 303 essentially form the pivot points 302. The locking slot 1016 is a captured recess that accommodates the internal slider plate 1028 extending from the back side of the locking slider 1020. The locking slot 1016 is below the thin finger bending region 1015 of the second finger lever arm 1012.

Figure 13A:
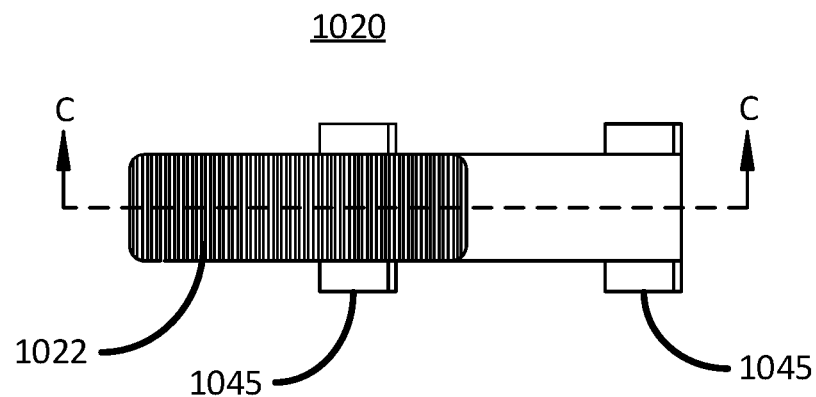
FIGS. 13A-13C show line drawings of different views of the locking slider consistent with embodiments of the present invention.
Figure 13B:
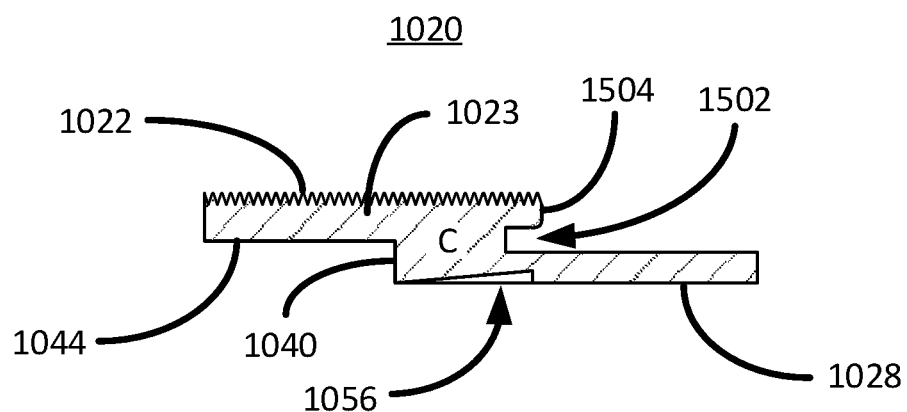
Figure 13C:
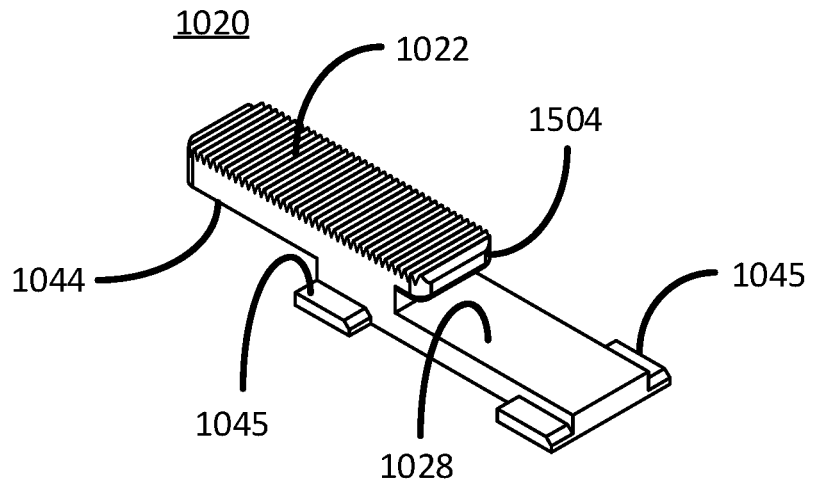

FIGS. 13A-13C show line drawings of different views of the locking slider 1020 consistent with embodiments of the present invention. FIG. 13A shows a front view line drawing of the locking slider 1020 with a cross-sectional cutline C-C bisecting the finger-gripping grooves 1022. Also shown in this perspective are the four captured tabs 1045. FIG. 13B shows the side view cross-section C from FIG. 13A. As shown in this view, the locking slider 1020 generally comprises an external fingerplate 1023 that extends upwardly from the internal slider plate 1028. The finger-gripping grooves 1022, used by a user's finger or thumb to move the locking slider 1020 in a locking position, essentially cover the length of the external fingerplate 1023. An arm facing surface 1044 is on the other side of the external fingerplate 1023 (on the obverse side of the finger-gripping grooves 1022). A retention tab channel 1502 is defined as a channel formed between a retention tab 1504 that extends from the external fingerplate 1023 over the internal slider plate 1028. The retention tab 1504 essentially performs the same function as the retention tab channel 502 of FIG. 7B. The internal slider plate 1028 comprises a wedge 1056 that terminates at a butting edge 1040, located under the external fingerplate 1023. FIG. 13C depicts an isometric line drawing view of the locking slider 1020 showing three of the four captured tabs 1045 that extends sideways from the internal slider plate 1020, the retention tab 1504 and the finger-gripping grooves 1022.

Figure 13D:
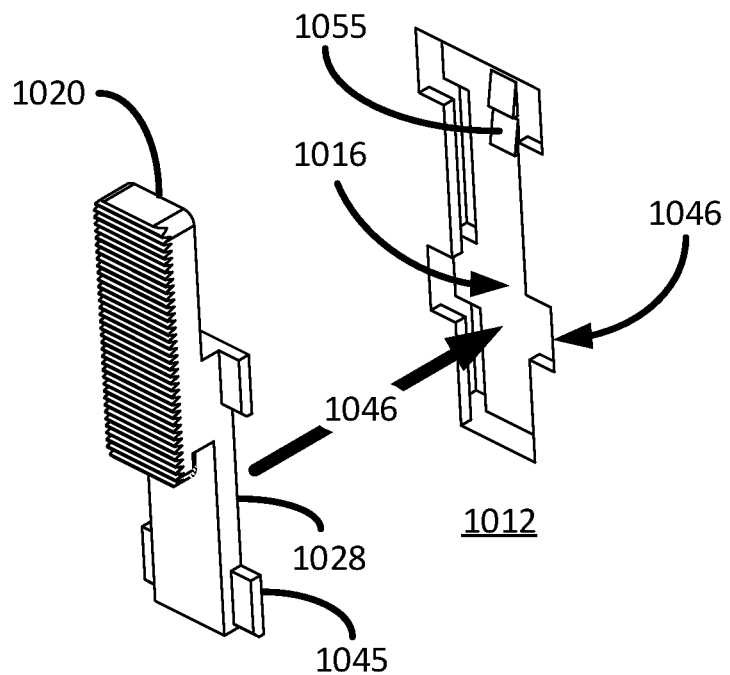
FIG. 13D illustratively depicts the isometric line drawing of the locking slider positioned for engagement with the locking slot consistent with embodiments of the present invention.

FIG. 13D illustratively depicts the isometric line drawing of the locking slider 1020 positioned for engagement 1046 with the locking slot 1016 consistent with embodiments of the present invention. As shown by the engaging arrow 1046, the internal slider plate 1028 fits into the locking slot 1016 like a puzzle piece when assembled. More specifically, the four captured tabs 1045 fit into the corresponding four tabbed openings/recesses in the second finger lever arm 1012. A locking slot 1016 is an opening that leads to an internal channel 1060 inside of the second finger lever arm 1012. A stacked pair of locking wedges 1055 are illustratively shown on the inner surface 1062 of the internal channel 1016.

FIGS. 14A and 14B are line drawings of a front view second finger lever arm 1012 and cross-section of the second finger lever arm 1012 in relation to the locking slider 1020 consistent with embodiments of the present invention. FIG. 14A shows the front view of the second finger lever arm 1012 with a cross-sectional cutline D-D running through the center of the locking slot 1016. The pivot hole 140, the thin finger bending region 1015 and the pivot apertures 303 are shown for reference.

FIG. 14B shows the cross-section D of the second finger lever arm 1012 and the locking slider 1020 (solid parts of the elements in crosshatch). With reference to the second finger lever arm 1012, shown therein is a cross-section view of the locking slot 1016, which is essentially a cavity 1017 that accommodates the locking slider 1020. The four captured tabs 1045 fits into the accommodating 1046 and the 1028 slides up and down in the locking slot cavity 1017. The receiving pivot aperture 303 and the pivot point aperture 140 are not shown in cross-section D.

Figure 15A:
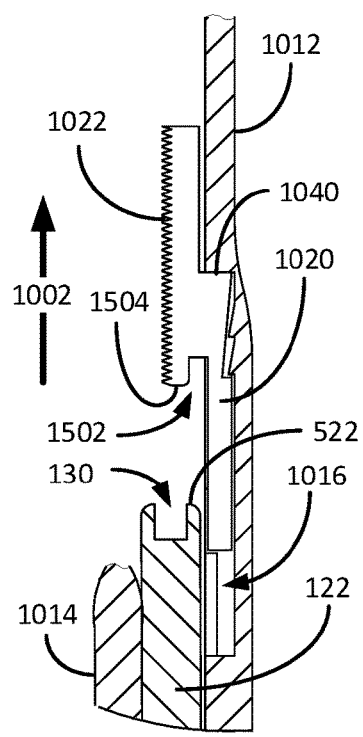
FIGS. 15A-15C illustratively depicts line drawings of various positions of a locking slider engaging a palm plate consistent with embodiments of the present invention.
Figure 15B:
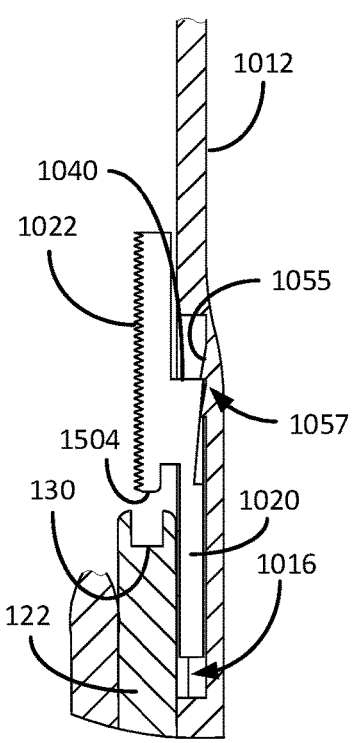
Figure 15C:
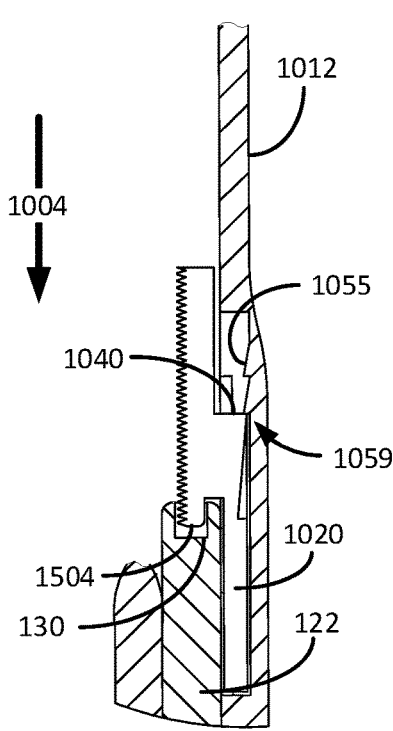

FIGS. 15A-15C illustratively depicts line drawing cross-sectioned views of various positions of a locking slider embodiment 1020 engaging a palm plate 122 consistent with embodiments of the present invention. FIG. 15A shows the locking slider 1020 arranged in an unlocked position 1002 wherein the locking slider 1020 is in an "up" position as indicated by the arrow 1002. With the locking slider 1020 in the unlocked position 1002, the secondary finger lever arm 1012 can freely move along the palm plate 122 without the potential of accidentally registering a cervix measurement. For example, certain embodiments envision a healthcare provider initially putting the cervix calipers 1000 on their hand 602 followed by then putting a glove over their hand 602 and the cervix calipers 1000. When in the unlocked position 1002, the cervix calipers 1000 are free to move with the healthcare worker's fingers without making the index finger lever arm 1014 ratchet to a cervix measurement number 125 thereby causing an accidental cervix measurement before actually taking a cervix measurement. As shown, when in the unlocked position 1002 the locking slider 1020 is separated from the palm plate 122. In other words, the retention tab 1504 is not engaged with the palm plate slot 130 and the retention tab channel 1502 is not engaged with the retention tab 1504. Also as shown, the slider butting edge 1040 is in the uppermost portion of the locking slot 1016.

FIG. 15B illustratively shows the locking slider 1020 locked against the locking wedges 1055 with the slider butting edge 1040 against the first wedge stop 1057. This can be accomplished by moving the locking slider 1020 downward towards the palm plate 122. Certain embodiments envision after the healthcare provider puts their glove over both their hand 602 and the cervix calipers 1000, the healthcare provider/worker slides the locking slider 1020 over the first locking wedge 1055 to lock the slider butting edge 1040 against the first wedge stop 1057. The first locking wedge 1055 is an intermediate wedge towards the final locking position shown in FIG. 15C.

FIG. 15C illustratively shows the locking slider 1020 locked against the first locking wedge 1055 with the slider butting edge 1040 against the wedge stop 1059 and fully engaged with the palm plate 122. When fully engaged with the palm plate 122, the retention tab 1504 is locked inside of the palm plate slot 130. This is accomplished by moving the locking slider 1020 fully downward 1004 to the palm plate 1022. Certain embodiments envision that after the healthcare provider moves the locking slider 1020 over the first locking wedge 1055, the healthcare provider fully engages the retention tab 1504 with the palm plate slot 130 effectively locking the slider butting edge 1040 against the second wedge stop 1059 of the second locking wedge 1055. With the locking slider 1020 locked fully downward 1004 (i.e., in an engaged relationship with the palm plate 1022), the healthcare provider can use the cervix calipers 1000 to intentionally take an actual cervix measurement.

With the present description in mind, below are a summary of some embodiments consistent with the present invention. The elements called out below are examples provided to assist in the understanding of the present invention and should not be considered limiting.

A cervix dilation caliper 100 comprising: a graduated palm plate 122 possessing on a first plate side 124 a female ratchet portion 115 and a plurality of graduated indicia 125; an index finger lever arm 104 pivotally attached to the first plate side 124 at a pivot point 140 in the graduated palm plate 122, a male portion 202 engaged with the female ratchet portion 115 and at least one of the graduated indicia 125 viewable via a window 120 in the index finger lever arm 104; a second finger lever arm 102 pivotally attached to a second plate side 124 of the graduated palm plate 122 at the pivot point 140, the cervix dilation caliper 100 configured to splay the index finger lever arm 104 and the second finger lever arm 102 apart like scissors; a first finger cuff 106 attached to an index finger distal end 136 of the index finger lever arm 104; and a second finger cuff 108 attached to a second finger distal end 137 of the second finger lever arm 102.

The cervix dilation caliper embodiment further contemplating wherein the male ratchet portion 202 comprises at least one pin 202 and the female ratchet portion 115 comprises a plurality of slots 115. This can further be defined wherein the plurality of slots 115 are arranged in an arc.

The cervix dilation caliper embodiment further envisioning wherein the male ratchet portion 202 comprises at least one ramped tooth 202 and the female ratchet portion 115 comprises a plurality of slots 115 that mate with the at least one ramped tooth 202, the at least one ramped tooth 202 only capable of moving along the plurality of slots 115 in one direction.

The cervix dilation caliper embodiment additionally envisioning wherein the male ratchet portion 202 is defined by at least one ramped tooth 202 that is defined by at least one ramped edge 210 and a trailing vertical edge 212, the trailing vertical edge 212 extends essentially orthogonally from the index finger lever arm 104. This embodiment can additionally be wherein the male ratchet portion 202 slidably engages the female ratchet portion 115 along the ramped edge 210 and lockingly engages the female ratchet portion 115 at the trailing vertical edge 212.

The cervix dilation caliper embodiment further contemplating wherein the graduated palm plate 122 has a plate leading edge 502 and a plate trailing edge 504, the second finger lever arm 102 comprises a retention tab 128 that retains the second finger lever arm 102 between the plate leading edge 502 and the plate trailing edge 504, the second finger lever arm 102 unconstrained to freely move between the leading edge and the trailing edge.

The cervix dilation caliper embodiment further envisioning wherein the first finger cuff 106 completes at least 270° of a circle with a slot 126 that is no more than 90° of the circle.

The cervix dilation caliper embodiment additionally envisioning wherein the first finger cuff 106 is less than 180° of a circle with a slot 126 that is no less than 180° of the circle.

The cervix dilation caliper embodiment additionally contemplating wherein the first finger cuff 106 is pivotally attached to the index finger lever arm 104.

The cervix dilation caliper embodiment further envisioning further comprising an index fingertip extender 112 extending distally from the first finger cuff 106 and second fingertip extender 110 extending distally from the second finger cuff 108. This embodiment can additionally defined wherein the index fingertip extender 112 and the second fingertip extender 110 are equal lengths.

The cervix dilation caliper embodiment additionally pondering wherein the index finger lever arm 104 and the second finger lever arm 102 are equal lengths.

Yet another embodiment of the present invention imagines a method comprising: providing a cervix caliper 100 possessing: a first finger arm 104 having a first proximal arm attachment region 134 and a first free distal region 136, a second finger arm 102 having a second proximal arm attachment region 134 and a second free distal region 137, the finger arms 102 104 pivotally attached to a palm plate 122 at a pivot point 140 at the proximal arm attachment regions 134; capturing a first finger 616 in a first finger cuff 106, the first finger cuff 106 attached to the first free distal region 136; capturing a second finger 614 in a second finger cuff 308, the second finger cuff 308 attached to the second free distal region 137; after the capturing steps, opening the cervix caliper 100 in a scissor motion by spreading the first finger 616 and the second finger 614 apart to touch a dilated cervix at approximately a largest diameter across the dilated cervix; reading an indicium 125 singled out from a set of graduated indicia 125 on the palm plate 122, the indicium 125 singled out via a one-way ratchet comprising a male ratchet component on the first finger arm 104 and a female ratchet component on the palm plate 124.

The method embodiment further comprising bending the first finger arm 104 and the second finger arm 102 at a plurality of finger bending grooves 116 disposed on the finger arms 102 104 when curling the fingers 614 and 616.

The method embodiment additionally imagining wherein the first finger arm 104 can only move in one direction along the palm plate 122 and the second finger arm 102 can move in two directions along the palm plate 122.

The method embodiment further proposing wherein at least the first finger cuff 106 is attached to the first free distal region 136 via a pivot pin 302, the first finger cuff 106 pivoting about the pivot pin 302.

The method embodiment further envisioning wherein the first finger 616 is an index finger and the second finger 614 is a middle finger.

Still another embodiment of the present invention proposes cervix dilation measurement caliper 100 comprising: a first finger lever arm 104 pivotally attached to a palm plate 122 in a first proximal region 134 of the first finger lever arm 104 via a pivot point 140; a second finger lever arm 102 pivotally attached to the palm plate 122 in a second proximal region 134 of the second finger lever arm 102 via the pivot point 140; a first finger cuff 106 attached to a first distal region 136 of the first finger lever arm 104, the first finger cuff 106 configured to capture a first human finger; a second finger cuff 108 attached to a second distal region 137 of the second finger lever arm 102, the second finger cuff 100 and a configured to capture a second human finger; at least one male ratchet protrusion 202 extending from the first finger lever arm 104, the male ratchet protrusion 202 mating with one of a plurality of female ratchet recessions 115 in the palm plate 122, the male ratchet protrusion 202 and the female ratchet recession 115 only permitting one way pivoting movement of the first finger lever arm 104 across the palm plate 122; and graduated indicia 125 displayed in a path following the plurality of female ratchet recession.

The above embodiments are not intended to be limiting to the scope of the invention whatsoever because many more embodiments are easily conceived within the teachings and scope of the instant specification. Moreover, the corresponding elements in the above example should not be considered limiting.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended embodiments are expressed. For example, though the embodiments teach finger cuffs and illustratively show their position, other embodiments envision different kinds of finger retention elements and in different locations which could equally be used while still maintaining substantially the same functionality without departing from the scope and spirit of the present invention. Other embodiments envision pointing to an indicium other than a window or arrow without departing from the scope and spirit of the present invention. While the embodiments herein are directed to a right hand using the cervix dilation calipers, the cervix dilation calipers can equally be used on the left hand with the 'index finger lever arm 104' being used on a second finger and the 'second finger lever arm 102' being used on the index finger without departing from the scope and spirit of the present invention. Though the calipers 100/300 can be worn without a glove, certain embodiments envision the calipers 100/300 intended to be worn inside of a protective medical glove within the scope and spirit of the present invention. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the appended claims.

What is claimed is:

1. A cervix dilation caliper comprising:
   a graduated palm plate defining a first plate side with a female ratchet portion and a plurality of graduated indicia;
   an index finger lever arm pivotally attached to the first plate side at a pivot point in the graduated palm plate, a male ratchet portion engaged with the female ratchet portion and at least one of the graduated indicia viewable via a window in the index finger lever arm;
   a second finger lever arm pivotally attached to a second plate side of the graduated palm plate at the pivot point, the cervix dilation caliper configured to splay the index finger lever arm and the second finger lever arm apart like scissors;
   a first finger cuff attached to an index finger distal end of the index finger lever arm; and
   a second finger cuff attached to a second finger distal end of the second finger lever arm.

2. The cervix dilation caliper of claim 1, wherein the male ratchet portion comprises at least one pin and the female ratchet portion comprises a plurality of slots.

3. The cervix dilation caliper of claim 2, wherein the plurality of slots are arranged in an arc.

4. The cervix dilation caliper of claim 1, wherein the male ratchet portion comprises at least one ramped tooth and the female ratchet portion comprises a plurality of slots that mate with the at least one ramped tooth, the at least one ramped tooth only capable of moving along the plurality of slots in one direction.

5. The cervix dilation caliper of claim 1, wherein the male ratchet portion is defined by at least one ramped tooth that is defined by at least one ramped edge and a trailing vertical edge, the trailing vertical edge extends essentially orthogonally from the index finger lever arm.

6. The cervix dilation caliper of claim 5, wherein the male ratchet portion slidably engages the female ratchet portion along the ramped edge and lockingly engages the female ratchet portion at the trailing vertical edge.

7. The cervix dilation caliper of claim 1, wherein the graduated palm plate has a plate leading edge and a plate trailing edge, the second finger lever arm comprises a retention tab that retains the second finger lever arm between the plate leading edge and the plate trailing edge, the second finger lever arm unconstrained to freely move between the leading edge and the trailing edge.

8. The cervix dilation caliper of claim 1, wherein the first finger cuff completes at least 270° of a circle with a slot that is no more than 90° of the circle.

9. The cervix dilation caliper of claim 1, wherein the first finger cuff is less than 180° of a circle with a slot that is no less than 180° of the circle.

10. The cervix dilation caliper of claim 1, wherein the first finger cuff is pivotally attached to the index finger lever arm.

11. The cervix dilation caliper of claim 1 further comprising an index fingertip extender extending distally from the first finger cuff and second fingertip extender extending distally from the second finger cuff.

12. The cervix dilation caliper of claim 11, wherein the index fingertip extender and the second fingertip extender are equal lengths.

13. The cervix dilation caliper of claim 1, wherein the cervical dilation calipers are disposed on an inside of a rubber glove, the cervical dilation calipers configured to be attached by a human hand and rubber glove adapted to cover the cervical dilation calipers and the human hand.

14. A method comprising:
   providing a cervix caliper possessing: a first finger arm having a first proximal arm attachment region and a first free distal region, a second finger arm having a second proximal arm attachment region and a second free distal region, the finger arms pivotally attached to a palm plate at a pivot point at the proximal arm attachment regions;
   capturing a first finger in a first finger cuff, the first finger cuff attached to the first free distal region;
   capturing a second finger in a second finger cuff, the second finger cuff attached to the second free distal region;
   after the capturing steps, opening the cervix caliper in a scissor motion by spreading the first finger and the second finger apart to touch a dilated cervix at approximately a largest diameter across the dilated cervix;
   reading an indicium singled out from a set of graduated indicia on the palm plate, the indicium singled out via a one-way ratchet comprising a male ratchet component on the first finger arm and a female ratchet component on the palm plate.

15. The method of claim 14 further comprising bending the first finger arm and the second finger arm at a plurality of finger bending grooves disposed on the finger arms when curling the fingers.

16. The method of claim 14 wherein the first finger arm can only move in one direction along the palm plate and the second finger arm can move in two directions along the palm plate.

17. The method of claim 14 wherein at least the first finger cuff is attached to the first free distal region via a pivot pin, the first finger cuff pivoting about the pivot pin.

18. The method of claim 14 wherein the first finger is an index finger and the second finger is a middle finger.

19. A cervix dilation measurement caliper comprising:
   a first finger lever arm pivotally attached to a palm plate in a first proximal region of the first finger lever arm via a pivot point;
   a second finger lever arm pivotally attached to the palm plate in a second proximal region of the second finger lever arm via the pivot point;
   a first finger cuff attached to a first distal region of the first finger lever arm, the first finger cuff configured to capture a first human finger;
   a second finger cuff attached to a second distal region of the second finger lever arm, the second finger cuff and a configured to capture a second human finger;
   at least one male ratchet protrusion extending from the first finger lever arm, the male ratchet protrusion mating with one of a plurality of female ratchet recessions in the palm plate, the male ratchet protrusion and the female ratchet recession only permitting one way pivoting movement of the first finger lever arm across the palm plate; and
   graduated indicia displayed in a path following the plurality of female ratchet recessions, the graduated indicia corresponding to different dilated cervix diameters, one of the graduated indicia configured to be singled out via the first finger lever arm when the cervix dilation measurement caliper is at least partially splayed to measure one of the different dilated cervix diameters.

20. The cervix dilation measurement caliper of claim 19, wherein the at least one male ratchet protrusion is a ramped tooth and the plurality of female ratchet recessions are slots in the palm plate.

* * * * *